United States Patent [19]

Wood et al.

[11] Patent Number: 5,715,823
[45] Date of Patent: Feb. 10, 1998

[54] ULTRASONIC DIAGNOSTIC IMAGING SYSTEM WITH UNIVERSAL ACCESS TO DIAGNOSTIC INFORMATION AND IMAGES

[75] Inventors: Michael A. Wood, Bothell; Pascal Roncalez, Bellevue; Lauren S. Pflugrath, Seattle; Jacques Souquet, Issaquah, all of Wash.

[73] Assignees: Atlantis Diagnostics International, L.L.C.; Advanced Technology Laboratories, Inc., both of Bothell, Wash.

[21] Appl. No.: 719,360

[22] Filed: Sep. 25, 1996

Related U.S. Application Data

[63] Continuation-in-part of Ser. No. 607,894, Feb. 27, 1996, Pat. No. 5,603,323.

[51] Int. Cl.[6] ............................................. A61B 8/00
[52] U.S. Cl. ............................ 128/660.01; 128/904
[58] Field of Search .......................... 395/601–615; 128/660.01, 903, 904

[56] References Cited

U.S. PATENT DOCUMENTS

| | | | |
|---|---|---|---|
| 4,545,251 | 10/1985 | Uchida et al. | 73/631 |
| 4,694,680 | 9/1987 | Tajeycgu et al. | 73/1 DV |
| 4,867,168 | 9/1989 | Stoor et al. | 128/653 |
| 4,958,283 | 9/1990 | Tawara et al. | 395/615 |
| 5,230,339 | 7/1993 | Charlebois | 128/660 |
| 5,329,445 | 7/1994 | Mukai | 395/615 |
| 5,469,353 | 11/1995 | Pinsky et al. | 395/601 |
| 5,642,513 | 6/1997 | Schnellinger et al. | 395/705 |

OTHER PUBLICATIONS

"Remote diagnostics can cut costs and downtime", G. Freiherr, *Diagnostic Imaging*, Feb. 1996.
"Computer Design," vol. 35, No. 8, Jul., 1996 at pp. 112, 121–122.
Brochure entitled "Access Image Management System, The Open Solution for Ultrasound Productivity, Performance and Economy" (1994).
"Access Acquisition Module" data sheet (1994).

*Primary Examiner*—George Manuel
*Attorney, Agent, or Firm*—W. Brinton Yorks, Jr.

[57] ABSTRACT

A medical ultrasonic diagnostic imaging system is provided which is capable of being accessed over data communication networks such as the Internet, making the ultrasonic images, diagnostic reports, and ultrasound system diagnostics information and operation accessible to a conventional personal computer using commercially available software at virtually any remote location. In one embodiment, the ultrasound system can be remotely operated from the personal computer. The inventive apparatus and techniques make it possible for physicians to remotely access, control, and perform diagnoses using their ultrasound systems over a network such as the World Wide Web with no special hardware requirements.

68 Claims, 17 Drawing Sheets

FIG. 7

```
  File  Edit  View  Go  Bookmarks  Options  Directory  Window          Tues 5:12
                                  Netscape: prtreport
 Back Forward Home  Edit  Reload Images Print Find Stop
 Location: http://699.59.9.114/cgi-bin/prtreport PT:                                             09/10/1996  Page 1/1
 OB   AUA:28w6d      EDD (AUA): 11/27/1996    EFW: 1567g(+/-229g)
                                                 3lb 7oz, 0%
      LMP:
     CI:    85%  ( . )   FL/AC:  26%  ( . )
     HC/AC: 1.00 ( . )   FL/BPD: 91%  ( . )

FETAL BIOMETRY
               #1       #2    #3    Mean        UA         %
     BPD(Had)  7.16a                7.16 cm   28w6d
     OFD(Han)  8.41a                8.41 cm   26w0d
     HC (Had) 24.53e               24.53 cm   26w5d
     AC (Had) 24.53e               24.53 cm   28w6d
     FL (Had)  6.50                 6.50 cm   33w4d Comments:
```

FIG. 9

```
 File  Edit  View  Go  Bookmarks  Options  Directory  Window                    Tues 5:14
                            Netscape: dodiag
Back Forward Home   Edit  Reload Images  Print  Find  Stop
Location: http://699.59.114/cgi-bin/dodiag?ConfigLog Tue Sep 10 17:07:23 1996    28 System Hw Config  PASSED  : System ID: 00000001f2e3d
Tue Sep 10 17:07:23 1996    51 System Sw Config  PASSED  : Software   : Integration
Tue Sep 10 17:07:23 1996  6928 VIO Config        PASSED  : VIO        : 7500-0969-00 at Address: 40000000
Tue Sep 10 17:07:24 1996  8628 BC Configuration  PASSED  : BC         : 7500-0886-04A
Tue Sep 10 17:07:25 1996  9228 SHS Config        PASSED  : SHS        : 7500-1092-02A
Tue Sep 10 17:07:26 1996  8928 HVPR Config       PASSED  : HVPR       : 7500-0889-02K
Tue Sep 10 17:07:26 1996  8719 CAM Sel. All Bds  PASSED  :
Tue Sep 10 17:07:27 1996  8730 CAM Config Step   PASSED  : CAM 0      : 7500-0887-05A
Tue Sep 10 17:07:27 1996  8730 CAM Config Step   PASSED  : CAM 1      : 7500-0887-05A
Tue Sep 10 17:07:28 1996  8730 CAM Config Step   PASSED  : CAM 2      : 7500-0887-05A
Tue Sep 10 17:07:29 1996  8730 CAM Config Step   PASSED  : CAM 3      : 7500-0887-05A
Tue Sep 10 17:07:29 1996  8728 CAM Config        PASSED  :
Tue Sep 10 17:07:30 1996  9828 DSP Config        PASSED  : DSP        : 7500-0098-03G           at Address: 60000000
Tue Sep 10 17:07:30 1996   319 Select All SHs    PASSED  : Left SH is missing;  Right SH  C4-2  40R   S/N  00DQM9, Date 951223, Cal 0.2
Tue Sep 10 17:07:33 1996   328 SH Config         PASSED  :
Tue Sep 10 17:07:33 1996     1 Configuration     PASSED  :
```

5,715,823

ULTRASONIC DIAGNOSTIC IMAGING SYSTEM WITH UNIVERSAL ACCESS TO DIAGNOSTIC INFORMATION AND IMAGES

This is a continuation in part of U.S. patent application Ser. No. 08/607,894 now U.S. Pat. No. 5,603,323.

This invention relates to improvements in ultrasonic diagnostic imaging systems which enable an ultrasound system to be accessed or controlled from a remote location.

U.S. Pat. No. 5,603,323 describes an ultrasound system which is quickly and easily upgraded from a remote location. Through two way communication with the ultrasound system, performance enhancements are remotely transmitted and installed without the need for a serviceman's call. The physician's diagnostic practice is enhanced by these quick and effective improvements to his or her ultrasound system. The present invention, among other things, provides a new technique for qualifying and testing such software upgrades for ultrasonic diagnostic systems worldwide.

An adjunctive business to ultrasonic diagnostic imaging which made an appearance in the 1990's is ultrasonic image management. Ultrasonic image management systems comprise specialized workstations, ultrasound system interfaces, ultrasound image storage devices and networks which are intended to facilitate ultrasonic diagnosis by the handling and storage of ultrasound images off-line. Such systems are intended to allow the physician to accumulate images in a storage medium for later recall from the workstation for review and diagnosis. While ultrasonic image management systems can offer a valuable capability for installations with multiple, intensively used ultrasound systems, they also require a considerable investment. The modules and workstations of an image management system usually have prices ranging in the thousands of dollars. Special installation is generally required and image management systems often employ proprietary hardware and software, which can act to limit their versatility. It is desirable to provide the advantages of an ultrasonic image management system without these numerous drawbacks.

In accordance with the principles of the present invention a medical diagnostic ultrasonic imaging system is provided which can be remotely accessed, interrogated or controlled from virtually any place on the globe to provide information about its operating characteristics, patient images and reports, or even for remotely controlled system operation. These capabilities may surprisingly be provided by commercially available software features and inexpensive personal computer hardware, making the capabilities easy to afford and use. Embodiments of the present invention describe techniques for modifying an ultrasonic diagnostic imaging system with inexpensive and readily available hardware and software, enabling the diagnostic information gathered through use of the ultrasound system to be accessed from remote locations. Constructed embodiments of the present invention are described which provide means for remotely accessing configuration information from the ultrasound system, running tests and diagnostics on the ultrasound system from remote locations, and even the ability to remotely control the operation of the ultrasound system. Embodiments of the present invention can also provide many of the functions and features of commercially available ultrasound image management systems, but for only a tiny fraction of the cost of a typical image management system.

A significant contribution of the ingenuity of the present invention resides in the adaptation of existing hardware and software to enable ultrasound systems to be accessed through an open architecture communication network, whereby image management capabilities may be provided through a conventional off-the-shelf personal computer with no special hardware, software, or expensive modifications.

In the drawings:

FIG. 7 illustrates a patient report Web page which is accessed through the patient directory Web page of FIG. 5 and displays an ultrasound image with no degradation in ultrasound image quality;

FIG. 9 illustrates a configuration log Web page which is accessed through the system diagnostics page of FIG. 8;

Figure 1:
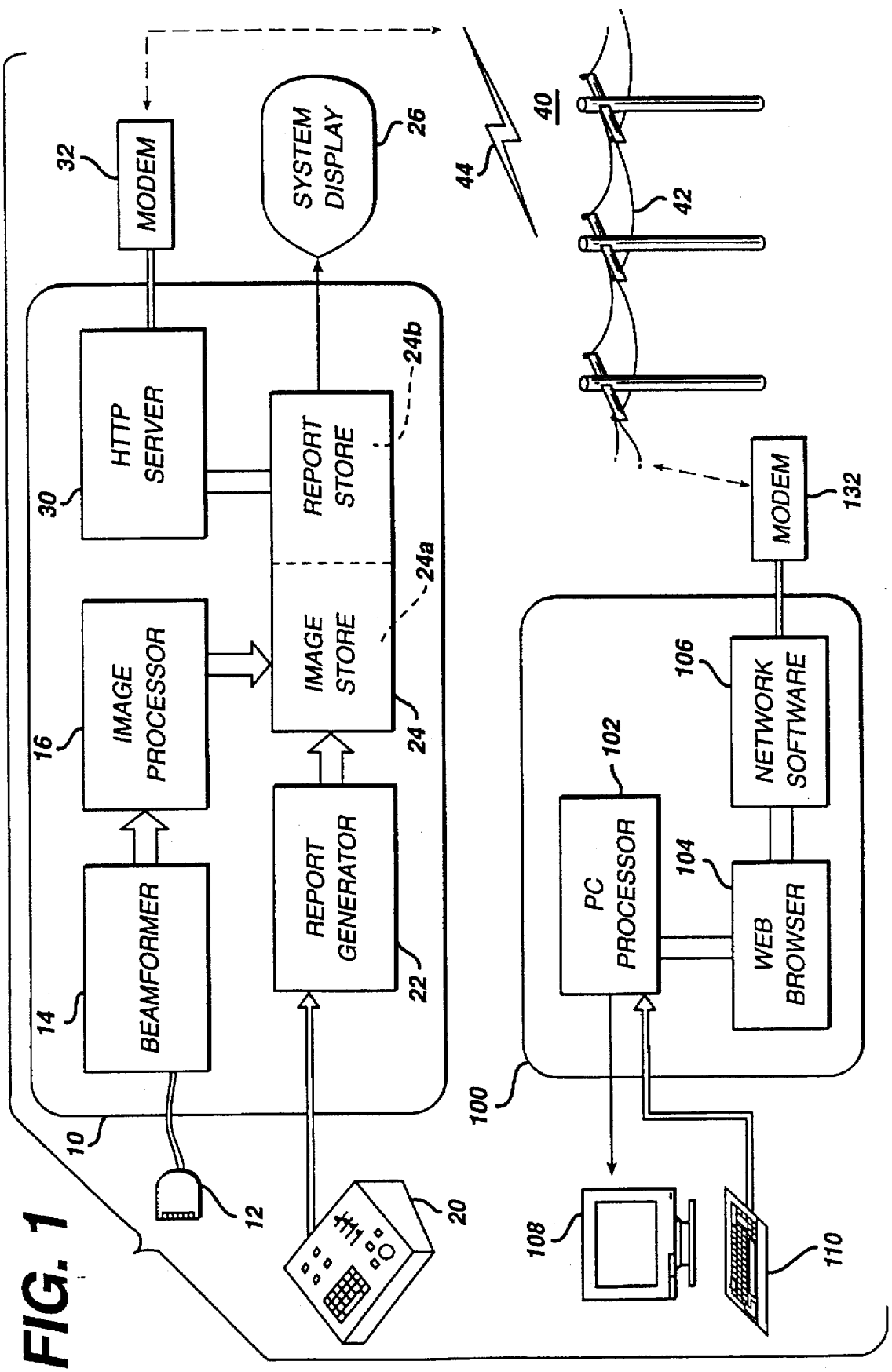
FIG. 1 illustrates in block diagram form an ultrasonic diagnostic imaging system which is constructed in accordance with the principles of the present invention to operate over an internetwork, together with a personal computer which can exchange diagnostic and ultrasound system control information with the ultrasound machine.

Turning first to FIG. 1, an ultrasonic diagnostic imaging system 10 which is constructed in accordance with the principles of the present invention is shown in the upper half of the drawing in block diagram form. The ultrasound system 10 is constructed to be accessed by a personal computer 100 which is remotely located. The ultrasound system 10 includes a number of conventional components, including a scanhead 12 which transmits ultrasonic waves into the body of a patient, receives echoes returning from the interaction of the transmitted waves with internal organs and tissue of the body, and converts the received echoes into electrical echo signals. The electrical echo signals are appropriately delayed and combined by a beamformer 12 to form coherent beams of echo information. The beams of echo information are processed by an image processor 16 to form ultrasonic images, which are stored in an image store partition 24a of a storage medium 24. The images may also be further processed by a video processor (not shown) to be placed in a raster format suitable for display on a system display 26.

The operation of the ultrasound system 10 is under the control of a control panel 20. The control panel 20 also enables a user to prepare diagnostic reports of the ultrasound exams performed, using a report generator software package 22 which is stored in the ultrasound system. The diagnostic reports may be displayed or printed out on a printer (not shown), and may also be stored in a report store partition 24b of the storage medium 24.

In accordance with the principles of the present invention the ultrasound system of FIG. 1 further includes a HyperText Transport Protocol (HTTP) server 30. The HTTP server is connected to access ultrasonic images and reports from the storage medium 24, and makes the system's images and reports accessible to a personal computer, terminal, or workstation at a remote location. In FIG. 1 the server 30 is connected by a modem 32 to a wire (42) or wireless (44) communication network 40. The server 30 makes the diagnostic information of the ultrasound system 10 available to users connected to access the ultrasound system through the communication network 40.

The terminal of one such user is shown in the lower half of FIG. 1. This user has a commercially available personal computer (PC) 100, including a PC processor 102, a monitor 108, and a keyboard 110. Installed on the personal computer 100 is a commercially available Web browser 104 and network software 106, which enable the user to access the World Wide Web of the Internet through a modem 132. The user is thus able to use the commercially available PC hardware and software to communicate over the Internet with the ultrasound system through the server 30.

The well known Internet is the result of developments known as internetwork technology, which enables computers and computer networks at one location to communicate with computers and computer networks at other locations. Basic development of internetworking technology began in the 1960's under the leadership of the Defense Advanced Research Projects Agency (DARPA) of the U.S. government, which was responding to the needs of scientists and the military to be able to exchange information over a computer network. Two basic approaches to communications networks were possible, circuit-switched networks and packet-switched networks. A circuit-switched network operates by forming a dedicated circuit between two points. An example of a circuit-switched network is the U.S. telephone network. Once a telephone caller has been connected to another telephone by switching technology, the capacity of that circuit is established and is not diminished by any other use of the network. Thus the advantage of circuit switching is a guarantee of capacity once the circuit is completed. The disadvantage is cost, for circuit costs are fixed, regardless of the level of network utilization.

Packet-switching employs a different approach. A message from one network user to another is broken up into discrete units of information called packets. The packets are directed across the network from the sender's location to that of the receiver by high speed routers which search the network for a pathway from sender to receiver. At the receiver's location the individual packets are received and reassembled to reform the original message. The advantage of packet-switching is that the network can handle many messages at one time by interleaving packets from different senders. The disadvantage of packet-switching is that as utilization of the network increases, higher volume traffic will slow the time required to send all of the packets of a message across the network.

The packet-switching approach became the choice for internetworked computers due to advantages of cost and performance. Since many computers can share a network and can communicate rapidly in short packet bursts, the costs of dedicated circuits are avoided. Moreover, demands for greater capacity are met by ever-increasing computer performance. Advances in computer technology provide the ability to handle higher volumes of data at ever increasing rates of data transfer.

DARPA's task was to connect numerous government and civilian computer networks in one unifying interconnection of networks, or internet. An internet is a group of interconnected networks that operate in a coordinated manner. Some of the most important developments which make internets possible came from research projects initiated by DARPA. This research had a very significant result: it established networking standards for packet-switching networks to communicate with each other, independent of the characteristics of their underlying hardware. These standards allow universal communication among computer networks, while allowing individual users to employ (or continue using) hardware of their own choosing. The common standards allow participants to individually employ and administer their own network hardware while seamlessly interacting with data from a universe of other users. This achievement led to the creation of the most famous internet connection, now commonly known as the Internet and its World Wide Web of interconnections. The present invention applies the Internet advantage of universal connectibility, and the benefits of the World Wide Web, to ultrasound to enhance the practice of diagnostic ultrasound by the physician and system serviceability by an ultrasound technician.

The Internet, as mentioned above, is a network of networks which facilitates the transfer of data among numerous users who are connected to the network. The World Wide Web (the "Web") is the name of a high level user interface which has been created on the Internet to make transfers of data easier and more logical. The Web provides users with a distributed menu system. Menu pages or screens are displayed to users through which the user can easily request information from another computer, or host. The major power of the Web is the ability to nonlinearly link or jump from one set of information to another through display elements called hypertext links. When a screen displays something in the characteristic of a hypertext link, generally blue text or a colored outline of a graphic, the user has the ability to click on the hypertext element and immediately be transferred to the data or information identified by the hypertext, whether the data is at the same host as the displayed information or at some other host location somewhere else in the world. The user has the ability to thereafter click back to the original screen display, or follow a sequence of links to sought-after information which can then be transmitted, or downloaded, from that host. On the Internet, Web addresses with the prefix "http://" denote Web screens with hypertext linking capability which conform to the published "RFC" standards of the Internet Engineering Task Force. Through hypertext linking a user is quickly able to follow pointers and references to the exact information being sought. The information returned through these links can be encoded to be reproduced in numerous formats, including text documents, images, graphics, video displays, and even audio. This power of the Web's hypertext linking is brought directly to ultrasound systems and diagnostic ultrasound information by the present invention.

Figure 2:
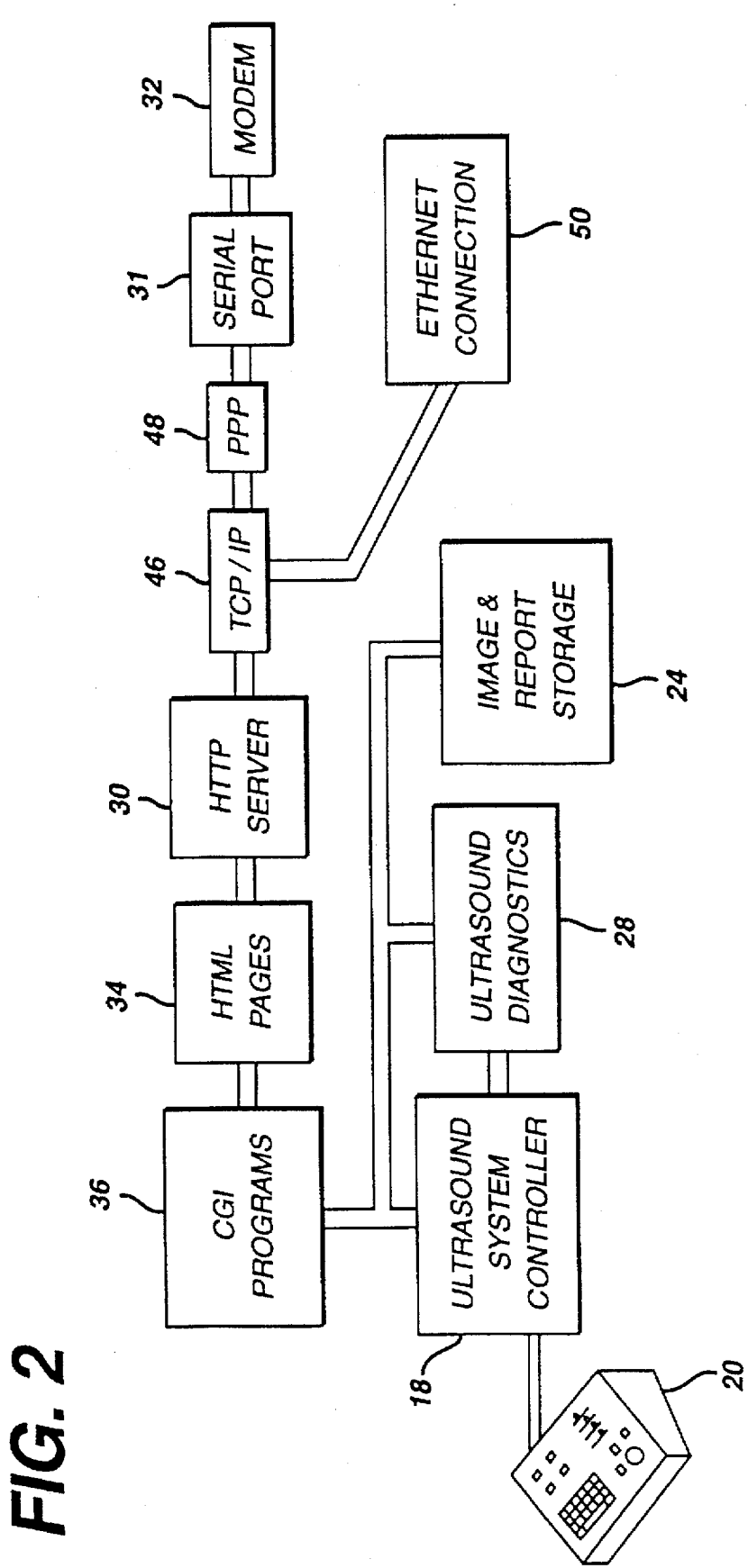
FIG. 2 illustrates in greater detail the internetworking components of the ultrasound machine of FIG. 1.

Turning now to FIG. 2, a more detailed block diagram of an ultrasound system constructed in accordance with the principles of the present invention is shown. The interface by which the system physically connects to the network is called a port. In FIG. 2 the ultrasound system is connected to an internetwork through a serial port 31. A common hardware device that translates between the digital domain of the ultrasound system and the analog domain of a telephone system is called a modem (modulator/demodulator). The modem 32 converts serial digital data from the serial port 31 into analog signals suitable for transmission over telephone lines. The modem also translates incoming analog telephone signals into digital data for passage through the serial port 31 and use by the ultrasound system. A suitable modem is available from Hayes Microcomputer Products, Inc., which has established standards used by a number of modem manufacturers.

Communication with the modem 32 is established by software known as PPP (point-to-point protocol) software as shown in block 48 of the drawing. PPP is a standard that enables multiple network protocols to be used over a modem line or other serial connection. Other standards can be used such as SLIP (Serial Line Internet Protocol), a standard that permits a communications protocol known as TCP/IP (discussed below) to be used over a modem line or other serial connection, or CSLIP (Compressed Serial Line Internet Protocol), a specialized form of SLIP. After the PPP software has been installed in the ultrasound system, it must be initialized or configured for the ultrasound system and modem with which it is operating. Configuration information controls the PPP software to be compatible with characteristics such as the serial port being used, the type of modem used, the phone line, host telephone number and dialing method, and login procedures and passwords. In general, the configuration information provides settings relating to initiating a network connection, when a connection is initiated, and what happens after a connection has been established. PPP software is incorporated in some operating system software packages such as Windows 95 from Microsoft Corporation of Redmond, Wash. for IBM-compatible PCs. PPP software for Apple personal computers is available from InterCon Systems Corporation of Herndon, Va., among others.

One of the accomplishments of the DARPA research project in internetworking was the establishment of a set of widely used network protocols called the TCP/IP Internet Protocol Suite. TCP/IP is named after its two most commonly used protocols, the Internet Protocol (IP) and the Transmission Control Protocol(TCP). The IP protocol controls the routing of data and the TCP protocol controls the transfer of data. TCP/IP provides a common means of interconnection through packet transfer devices known as gateways. A gateway is a specialized internetworking computer that connects two or more networks and routes packets of data between them.

When the ultrasound system has data it wishes to transfer over the Internet, the data is passed to TCP/IP as shown in block 46 of the drawing. TCP encapsulates data into segments called TCP packets with header information that is used to track, check and order the data segments in the proper sequence. Since a block of data is transmitted over the Internet in discrete packets, individual ones of which may be routed differently by gateways, there is no assurance that the packets will arrive at their destination in the proper order or without errors. The TCP packets provide a means of assuring packet delivery, integrity, and sorting order. At the receiving end the packets are checked for errors in accordance with the TCP packet header information, error-free segments are acknowledged, and the packets are put in order to reassemble the original block of data. The sender keeps track of segment acknowledgments, and if a segment is not timely acknowledged the sender retransmits the packet. If a segment is lost on initial transmission or received out of order, TCP holds the received segments until all segments are accounted for at the received end, at which time they may be ordered in their proper and complete sequence for reassembly of the original block of data.

At the transmitting end, TCP packets are passed to IP, which puts the segments into the form of IP packets or datagrams. The datagram contains an IP header which provides addressing information used by gateways to route the datagram to its proper destination. The IP header contains the source and destination Internet addresses to enable gateways to properly route the data, and the receiver to acknowledge receipt of the datagram. IP makes a best-effort attempt to deliver all datagrams, but does not assure their delivery. Assurance of delivery is provided by TCP through acknowledgment and retransmission as described above.

Like the PPP software, the TCP/IP needs to be configured for the particular ultrasound system and its environment. Typical configuration information for TCP/IP includes information on the type of local network if the ultrasound system is locally networked with other ultrasound machines (e.g., Ethernet or token ring network), information as to the addresses of other systems on the local network, the gateway address if the system is performing a router function, the user name of the ultrasound machine and access password, the address of the servers on the ultrasound system, the Internet address (IP address) for the ultrasound system, and the default domain for the local network. Like PPP, TCP/IP software also comes with some system software packages such as Windows 95, and is available for Apple computers from InterCon.

A key to successful operation of any internet, and the Internet in particular, is the need for a unique address for every system, or "host," which is directly connected to the internet. Every user which connects directly to the Internet must obtain an IP address from a central authority known as the Network Information Center (NIC), which utilizes computerized mediation to assign IP addresses to those requesting them. An IP address is 32 bits in length, and is expressed in four decimal notations of groups of eight bits, separated by periods, such as 699.59.9.114 (an invalid IP address used as an example herein). IP addresses are classed by the size of the network connected to the Internet, with Class A addresses reserved for very large networks, Class B addresses for medium-sized networks (255 to 65,000 users) such as a university network, and Class C addresses for small networks (less than 256 users) such as a radiology clinic or hospital. Significantly, IP addresses do not specify an individual computer or machine; rather, they specify a connection to the Internet. If an ultrasound machine has two network connections to the Internet, each must have a unique IP address. A corollary of this aspect is that a local network can employ subnetwork addressing in which each local machine has a subnetwork address, with the network being connected to the Internet at a single host connection with an IP address which provides access for all local systems to the Internet. Subnetwork addressing is permissible when the subaddresses of the network are not visible to users of the Internet itself.

Another type of permitted Internet addressing which the NIC administers is domain name addressing. Since many users would prefer being addressed by meaningful words of a language rather than numbers, the NIC can assign a user a domain and a subdomain name, with the user free to add further subdomain names for which it has mapping responsibility for its network. The domain is the major classification, with commercial users being assigned the domain name COM, educational institutions the domain name EDU, government institutions the domain name GOV, and so forth. A hypothetical domain name for the ultrasound department of a Veterans Administration hospital owned by the U.S. government might be ULTRASOUND.VAHOSPITAL.GOV, for instance.

In FIG. 2 TCP/IP is connected to a local network medium, in this case an Ethernet connection 50. The Ethernet connection 50 connects the ultrasound system to other systems on a local network. In an Ethernet network the systems on the network must be within a maximum allowable distance of each other and are all connected to the same physical network wiring. Data can be transmitted on the Ethernet network at high speed (previously 10 Megabits per second; current versions have speeds of up to 100 Megabits per second), with each system permitted to transmit only when no other system is currently transmitting over the system. A technique called Carrier Sense Multiple Access with Collision Avoidance (CSMA/CA) prevents two systems from using the network wiring simultaneously. The ultrasound system may be connected in other types of local networks such as a token ring network, in which all systems are connected in a continuous chain which passes information through every system on the network. TCP/IP is configured in the illustrated embodiment for communication over the local Ethernet, or over the worldwide Internet.

Interacting with the TCP/IP and PPP network software is the HTTP server 30. The HTTP server is a software program with which a Web browser communicates to access information from the ultrasound system. The HTTP server responds to external requests by displaying Web pages of information and hypertext connections to additional Web pages and information such as ultrasound images and reports. The HTTP server also responds to external requests to perform a specific action associated with a button or control on the ultrasound system, as described more fully below.

A constructed embodiment of the present invention uses a popular Web server known as Apache, which was compiled and installed on the ultrasound system. The Apache server is public domain software which may be downloaded from the Internet at the address http://www.apache.org/, and conforms to NCSA standards. Care must be taken when downloading software, particularly for commercial use, so that the copyright laws and the rights of software owners and developers are properly observed.

The server, like the previously described software, must be specially configured for the ultrasound system. The Apache server has over 250 directives for configuring the server for its intended application. One important configuration file of Apache deals with security. This configuration file controls the access of outsiders to elements of and information on the ultrasound system. Access may be limited to specified drives, directories and files of the ultrasound system, and limited to reading only. Access may also be restricted to certain users and certain numbers of simultaneous users, and passwords required. The server records the location of the logfile, the file of users who have accessed the system. The configuration files identify the port number used by the server and the administrator of the server. The configuration files store the location of files used by the server, including the server root directory and the addresses of Web pages and CGI programs (described below) which are used by the server. Other characteristics for which the server may be configured include such features as multilingual capability.

In response to external requests the HTTP server 30 transmits HyperText Markup Language (HTML) pages 34 to an inquiring Web browser. HTML pages describe what the Web browser will display on the screen at the remote terminal, including buttons, text, images, animated real time loops of images, sounds, and so forth. HTML pages may be directly encoded in software by following the instruction published in a number of reference texts such as *HTML* and *CGI Unleashed*, by John December and Mark Ginsburg, published by Sams.net Publishing, Indianapolis, Ind. Simple HTML pages may be written using commercially available desk-top publishing and word processing software, then encoded in HTML form using software known as the Internet Assistant, which may be downloaded through Microsoft's homepage at www.microsoft.com. Alternatively, public domain software known as "Webmaker" may be downloaded from the Internet and used to make Web pages. Web pages contain HTML tags of data which describe how the page is to be interpreted by a Web browser at the remote terminal. Links to ultrasound image files are provided by IMG tags in the Web page code. An HREF hypertext reference provides a means for linking to other Web pages on the same ultrasound machine, or to Web pages on any other host machine on the network or Web. Once the HTML pages are created they are copied to the ultrasound machine and their storage addresses provided to the HTTP server. Whenever a remote terminal asks to view a particular Web page of the ultrasound machine, the HTTP server 30 is responsible for finding the page and sending its contents back to the requester.

The ultrasound system of FIG. 2 includes a number of small executable programs called Common Gateway Interface (CGI) programs as shown at 36. The CGI programs provide an interface between the HTML pages and the hardware and software of the ultrasound system. The CGI programs communicate with the ultrasound system, asking the system to perform actions or provide requested information such as images, reports, or current status. In a constructed embodiment the CGI programs respond to external requests for information by dynamically creating custom HTML pages in which the requested information is embedded. The following examples illustrate the operation of CGI programs that provide patient directories of ultrasound images and reports (patdir), display of a selected ultrasound image (dispimage), general purpose programs that execute tasks in response to input arguments (doaction), perform system diagnostics (dodiag), and provide patient directories for a number of ultrasound machines on a network (serverdir).

The CGI programs in the constructed embodiment are stored on the ultrasound system's hard disk in a directory called "cgi-bin." In performing their operations the CGI programs access ultrasound images and reports which are stored at 24, accesses and executes diagnostic routines stored at 28, and interacts with the controls of the ultrasound system through the ultrasound system controller 18. As an example of a CGI program, Table 1 illustrates the coding of a CGI program which fetches an ultrasound image and embeds the image in an HTML page. In the constructed embodiment the CGI programs are compiled in the C language for speed of execution and security from remote tampering. CGI programs can also be used to format ultrasound images into a data format that is compatible with Web pages. In the constructed embodiment such reformatting is not necessary, however, since the ultrasound system is designed to store ultrasound images in the GIF (Graphic Interchange Format) format, an image format which can be read by most Web browsers.

Figure 3:
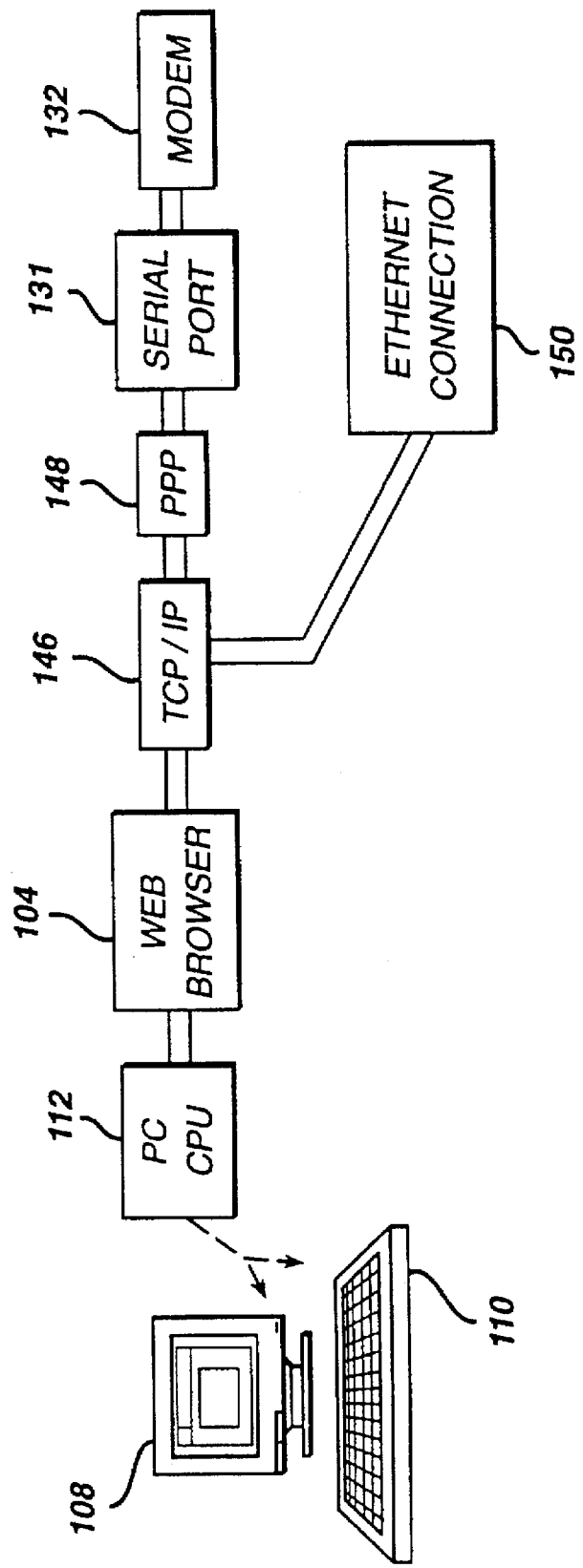
FIG. 3 illustrates in greater detail the internetworking components of the personal computer of FIG. 1.

The specially modified ultrasound system of FIG. 2 can be accessed by a standard Internet compatible personal computer terminal as shown in FIG. 3. The personal computer central processing unit (CPU) executes the PC's software in response to actions on the keyboard 110 and mouse (not shown) and displays ultrasound data and images on the screen of the monitor 108. The CPU executes the Web browser software 104 to access the Internet through TCP/IP and PPP protocols 146 and 148 configured for the personal computer. Connection to a network is through the PC's serial port 131 and a modem 132. The PC may be networked to other devices through an Ethernet connection 150. The TCP/IP and PPP may be obtained from the sources listed above. The Web browser software 104 may be obtained from Netscape Communications Corporation of Mountain View, Calif. or the Internet Explorer browser may be obtained from Microsoft Corporation and is generally included with Windows 95 operating software. It is seen that no special hardware or software beyond that which is readily commercially available is needed to access the ultrasound system of the present invention.

Some examples of the use of an ultrasound system constructed in accordance with the principles of the present invention are shown with reference to FIGS. 4 through 14. These figures, except for reference numerals and the exemplary IP address, are actual prints of Web browser screens taken while the browser of a remote terminal was in communication with a constructed embodiment of the present invention.

Figure 4:
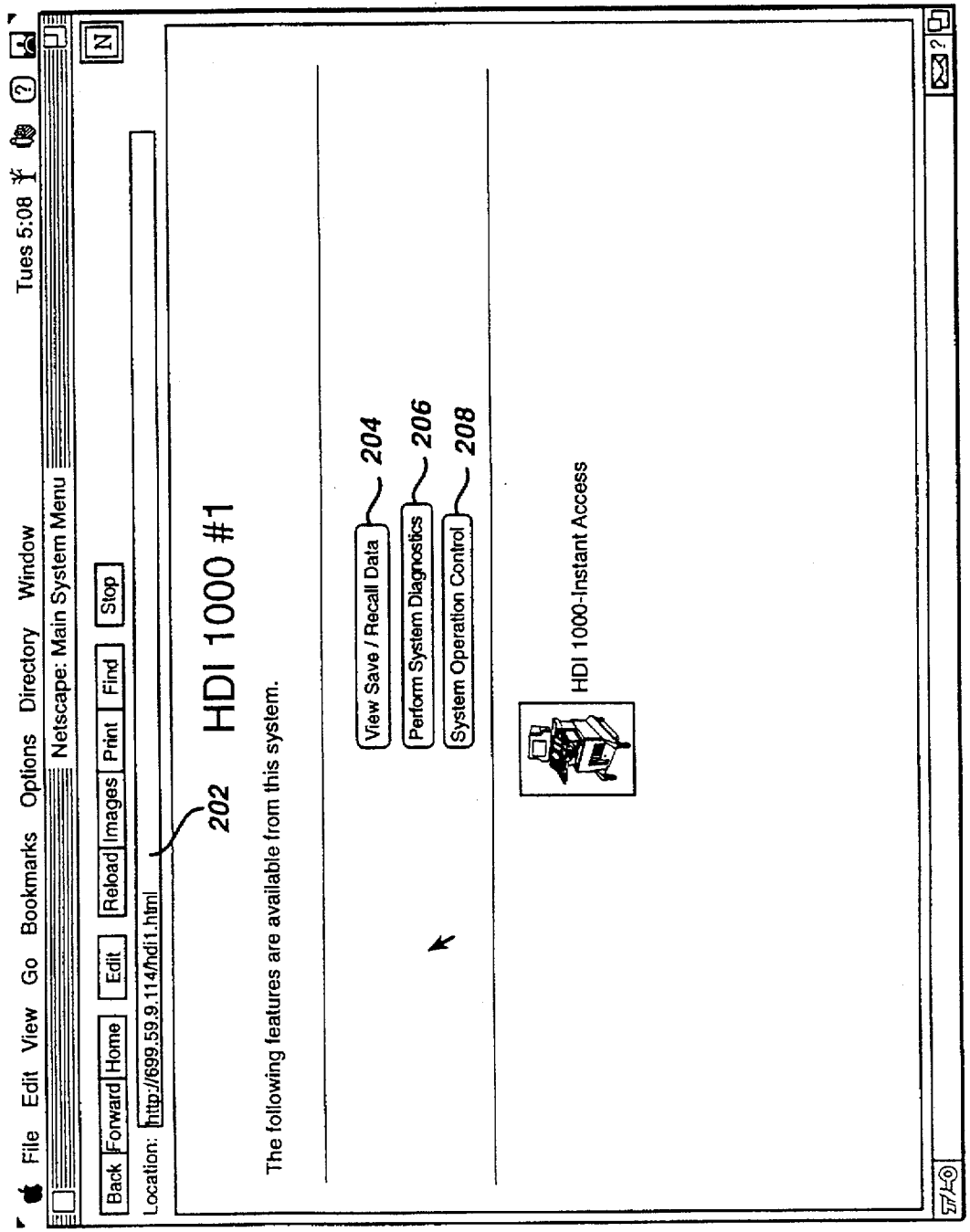
FIG. 4 illustrates a Web home page of an ultrasound system constructed in accordance with the principles of the present invention as it appears when accessed over an internet from a remotely located personal computer or terminal.

FIG. 4 shows the home Web page of an ultrasound system constructed in accordance with the present invention and identified as HDI 1000 #1. As the figure shows, this Web homepage was acquired by a Netscape Web browser. The usual browser control buttons are seen above the Web URL indicator 202. The URL indicator 202 shows the address used to contact ultrasound system HDI 1000 #1, which is http://699.59.9,114/hdi1.html. The html suffix on the address denotes the display as a hypertext Web page.

Figure 5:
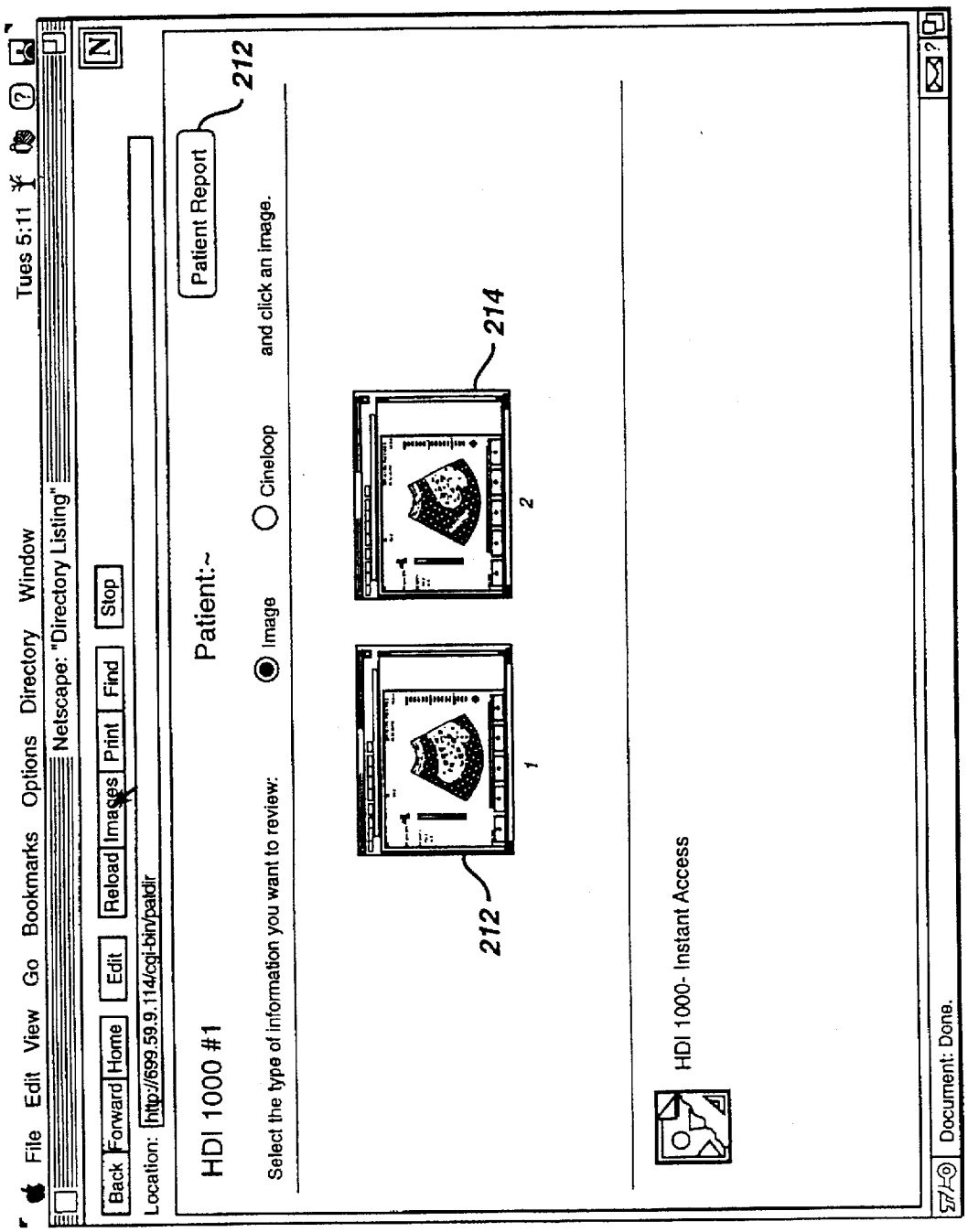
FIG. 5 illustrates a patient directory Web page for a specific patient which is accessed through the Web home page of FIG. 4.
Figure 6:
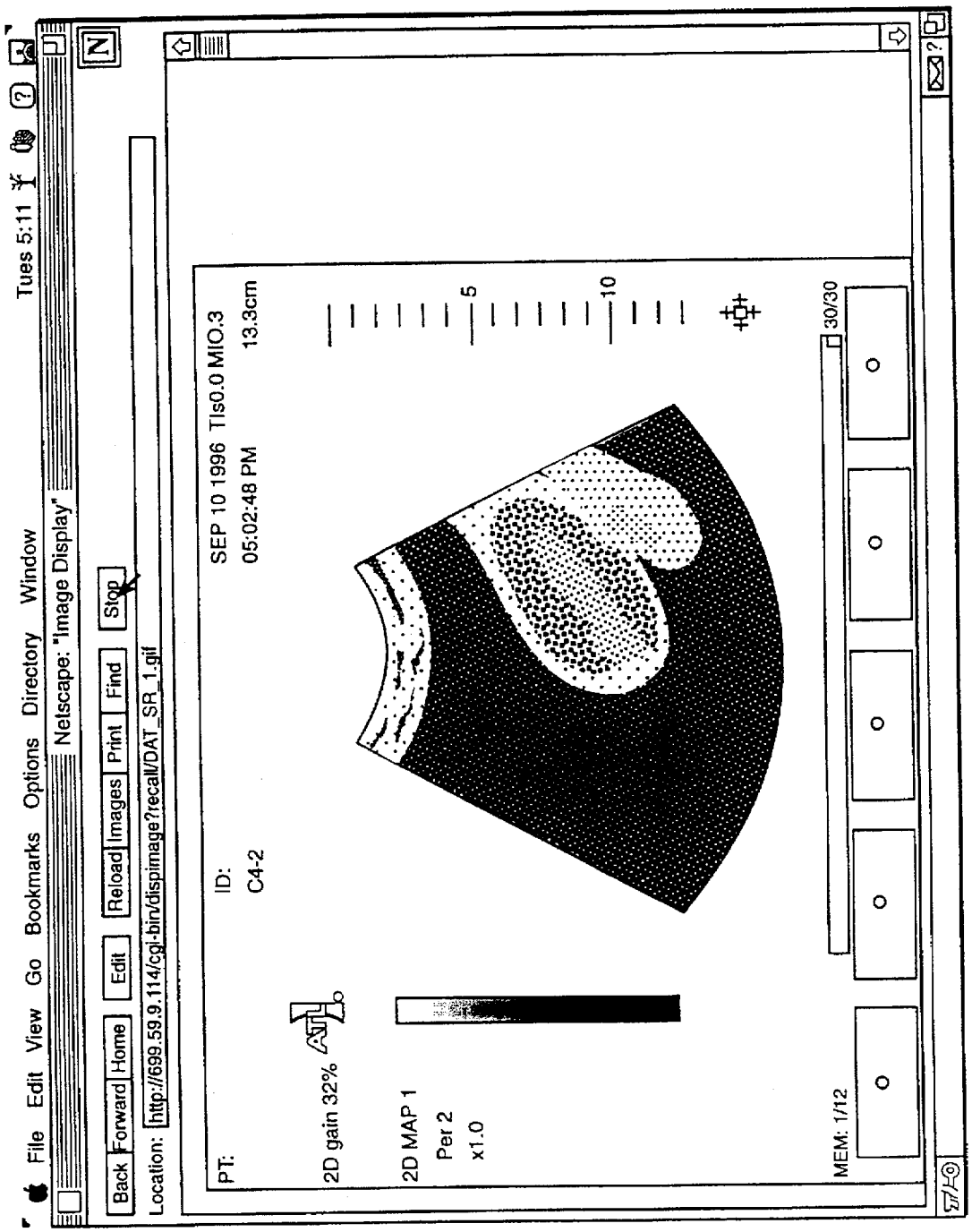
FIG. 6 illustrates an ultrasound image Web page which is accessed through the patient directory Web page of FIG. 5.

In the center of the homepage of FIG. 4 are three hypertext buttons providing links to other ultrasound information or controls. When the user at the remote terminal clicks the first button 204 with a computer mouse or keyboard key, View Save/Recall Data, a CGI program "patdir" is executed which creates a patient information Web page in which ultrasound images of the patient are embedded and a hypertext link provided to patient reports on that patient. This patient directory Web page is shown in FIG. 5. This Web page contains two small ultrasound images 212 and 214 which were obtained from the ultrasound system's image store 24a. The remote terminal user may click on either of these small images to see a full size rendering of the image with its original image quality, or play the real time image sequence represented by the small image. The remote terminal makes an election of these options by clicking on the "Image" or "Cineloop" options above the small images. When the remote terminal user clicks on "Image" and then on the small image 212, the HTTP server 30 of the ultrasound system returns a Web page with a large rendition of the selected image as shown in FIG. 6. The address bar in FIG. 6 shows that the ultrasound system has transmitted an image identified as "DAT_SR_1", which is stored in the "GIF" image format. For speed of transmission the small images of the patient directory of FIG. 5 can be compressed and readable in accordance with the JPEG standard, whereas the full size image of FIG. 6 is transmitted without loss of image quality using the GIF image format By clicking on the browser's "Back" button at the upper left of FIG. 6 the remote terminal user returns to the Web page of FIG. 5. The remote terminal user can now click on the Patient Report button 216. In response to activation of this hypertext link button, the HTTP server 30 causes the execution of a CGI program called "prtreport," which retrieves diagnostic reports for the identified patient which are stored in storage 24b and embeds them in a Web page for transmission by the server. The server returns the Web page shown in FIG. 7, which contains patient report information. The Internet functionality which is brought to ultrasound by the present invention provides a further feature, which is the capability for the remote terminal user to fashion a new patient report or edit an old one. On the same terminal the remote terminal user opens a word processing application. Using the "Edit" feature at the top of the browser in FIGS. 6 and 7, the remote terminal user copies the ultrasound image and the patient report, and in turn pastes them into a word processing document. The remote terminal user can, for instance, paste the ultrasound image first, then the patient report below the image. The user can then edit the text file of the patient report, modifying the received report or creating a new one. Using graphics features of the word processing program the remote terminal user can circle, draw on, or point to specific features of the ultrasound image for easy reference from the report. The new report can be filed away on the remote terminal or to a remote location, or even e-mailed over the Internet directly from the remote user's terminal to a referring physician. Additionally, the patient report with its images can be printed out directly from a computer printer connected to the remote user's terminal.

Using the Back button again (or an appropriate hyperlink), the remote terminal user can return to the homepage of FIG. 4. When the remote terminal user clicks on the second hypertext button 206, Perform System Diagnostics, the HTTP server 30 transmits the linked system diagnostics menu Web page shown in FIG. 8. Each of the hypertext linked buttons on the system diagnostics menu will cause the execution of a CGI program "dodiag" with a different argument, which causes the ultrasound system to perform a system diagnostic or display system status information such as test and error logs. These remote control functions are desirable when performing remote diagnosis of the operability of the ultrasound system. For instance, clicking on button 222, Perform Configuration Test, causes the dodiag CGI program to execute the ultrasound system's stored ultrasound diagnostic routines 28 and return a Web page containing a log of the results of those tests as shown in FIG. 9.

The ability to perform diagnostic tests on the ultrasound system remotely is especially useful following the remote installation of ultrasound software upgrades. After the new software is installed, this capability is used to execute a system diagnostic routine which exercises the new software and validates its performance. As in FIG. 9, the results of these validation tests are returned to the remotely located installer, verifying the successful installation of the new software.

Figure 8:
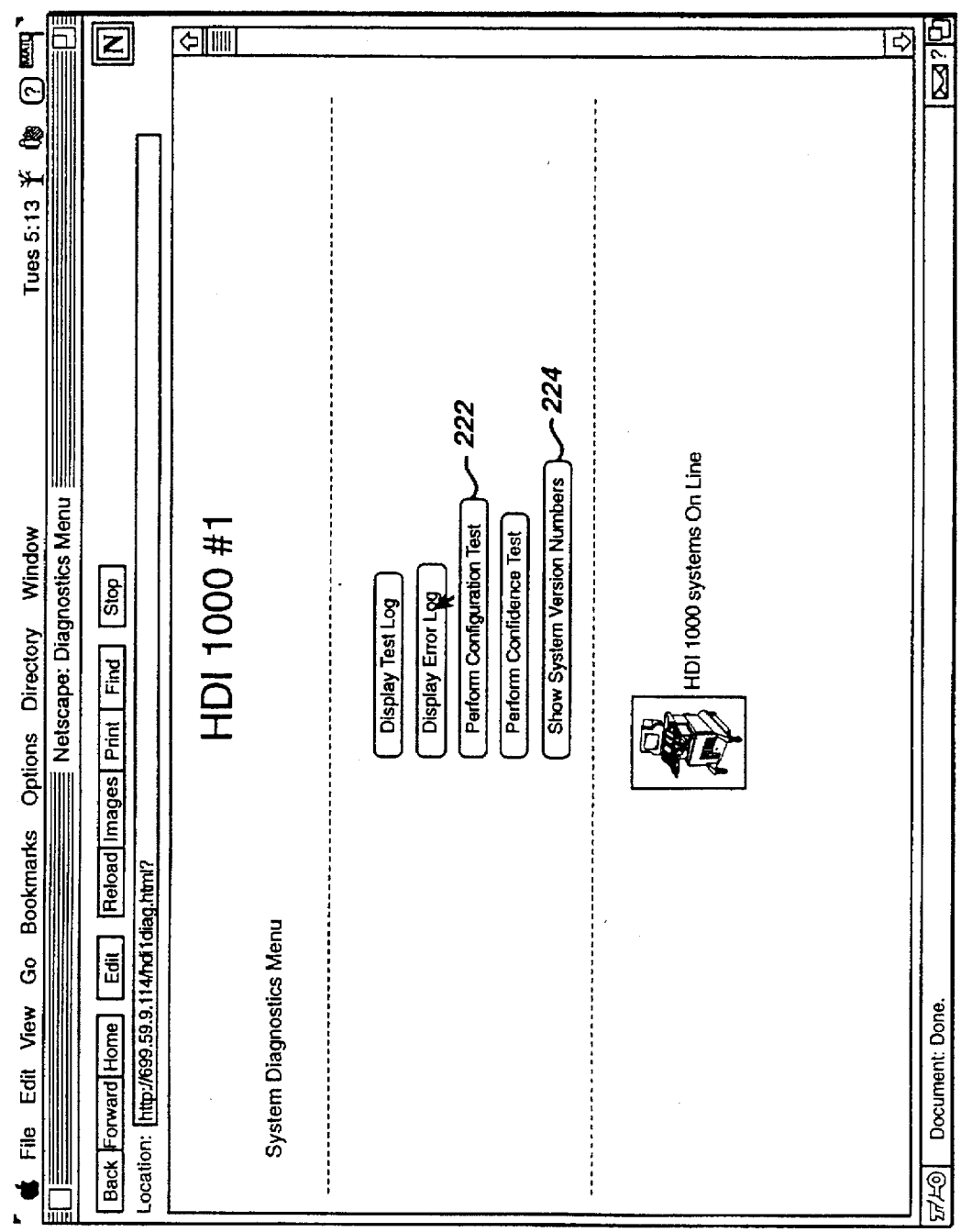
FIG. 8 illustrates the main menu of a system diagnostics Web page which is accessed through the Web home page of FIG. 4.

Another capability of the system diagnostics menu of FIG. 8 which is especially useful for ultrasound software upgrades is button 224, Show System Version Numbers. Clicking on this button causes the ultrasound diagnostics programs to return the level or version numbers of the software installed in the ultrasound system. Knowing the current version or level of the ultrasound system software is a necessary prerequisite to the installation of any ultrasound system upgrade.

The Perform System Diagnostics functions can be performed by an on-site serviceman using a laptop computer. When the serviceman is with the ultrasound system, there is no need for modem interconnection; the network link can be made directly. In this case a cable is connected from the serial port 131 of the laptop computer (FIG. 3) to the serial port 31 of the ultrasound system (FIG. 2). Alternately, of course, the Ethernet connections 50 and 150 could be interconnected. In either case, access and interrogation of the ultrasound system by the repairman proceeds as described above, but at the much faster data rate of a direct network connection. Thus, a visiting serviceman can use his laptop computer to perform system diagnostics, check error logs, verify configurations and software levels, and other system maintenance and repair activities.

Figure 10:
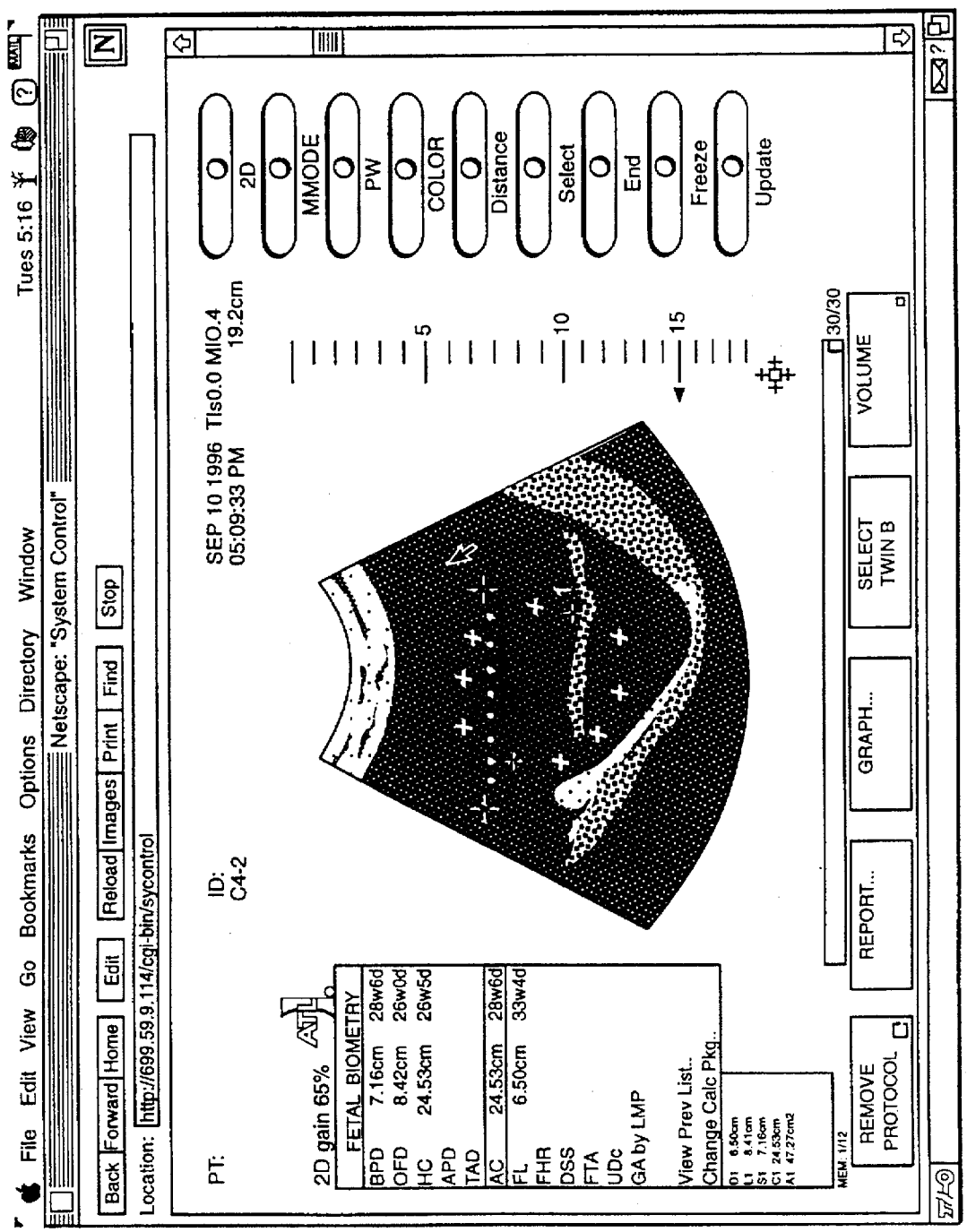
FIG. 10 illustrates a system control Web page which is accessed through the Web home page of FIG. 4.

Clicking Back to the ultrasound system's homepage of FIG. 4, it is seen that a third hypertext button 208 is available, System Operation Control. Clicking on this button 208 causes the HTTP server 30 to execute a CGI program called "syscontrol". The syscontrol CGI program creates a Web page in which is embedded the ultrasound image most recently produced by the ultrasound system as shown in the center of FIG. 10. To the right of and below the ultrasound image are displayed user controls of the ultrasound system. The displayed controls of the ultrasound system are all hypertext graphics. Clicking on these buttons causes the syscontrol CGI program to command the ultrasound system controller 18 to change the operation of the ultrasound system in accordance with the function of the selected control. In the constructed embodiment the buttons to the right of the ultrasound image depict the system's hardkey mode control switches, and the buttons below the image depict softkey controls used to change system parameters operable in the selected mode. The lowest depicted hardkey, Update, is not an ultrasound system control, but a control for this remote control feature of the present invention. Clicking on Update will cause the HTTP server and CGI programs of the ultrasound system to update the remotely displayed image with the ultrasound image produced most recently by the ultrasound system.

These capabilities mean that a physician can perform an ultrasound exam from distances of thousands of miles from the patient, needing only a pair of hands at the patient's location to hold and manipulate the ultrasound probe. The skills of eminent radiologists and echocardiologists can now be brought to bear on a diagnostic situation anywhere in the world. Any EMT or medical corpsman can hold and manipulate the probe as directed by the remotely located physician while the physician controls the operation of the machine to produce the best, most diagnostic ultrasound image. Since the Internet connection can send and receive audio as well as video information, the instructions of the physician to the holder of the ultrasound probe can be sent over the same Internet connection as the ultrasound information. The physician can switch back and forth between the 2D and Color modes or any other desired mode, alternately studying tissue structure and blood flow conditions. In another embodiment the physician could switch between individual 2D images of a sequence of spatially different images and the 3D mode, where the sequence of spatially discrete images can be rendered in a three dimensional presentation. Difficult diagnostic cases can be directed to the most appropriate specialist for that case type on a moment's notice. Telemedicine embraces telexamination, as the reach of the diagnosing physician is now unbounded by geography.

In the constructed embodiment, the ultrasound system itself is based upon a personal computer architecture and carries out the functions of the ultrasound machine with a multi-tasking operating system, as described in U.S. patent application Ser. No. 08/712,828, filed Sep. 12, 1996. This operating architecture makes it possible for the ultrasound system to be used for diagnostic exams in the normal manner while a remote terminal user simultaneously interrogates the ultrasound system for images, reports, and information. The multi-tasking operating system enables the central processor of the ultrasound system to carry out normal ultrasonic imaging tasks and network communications tasks in a time interleaved manner. To the operator at the system and the interrogator at the remote terminal, their separate functions appear to each of them to be executed in real time, without conflict with the activities of the other. This means, for instance, that a physician can monitor the progress of an ultrasonographer operating the ultrasound system, retrieving images for diagnosis and patient reports from the ultrasound system for one patient while the ultrasonographer is in the process of conducting a diagnostic examination of another patient.

Figure 11:
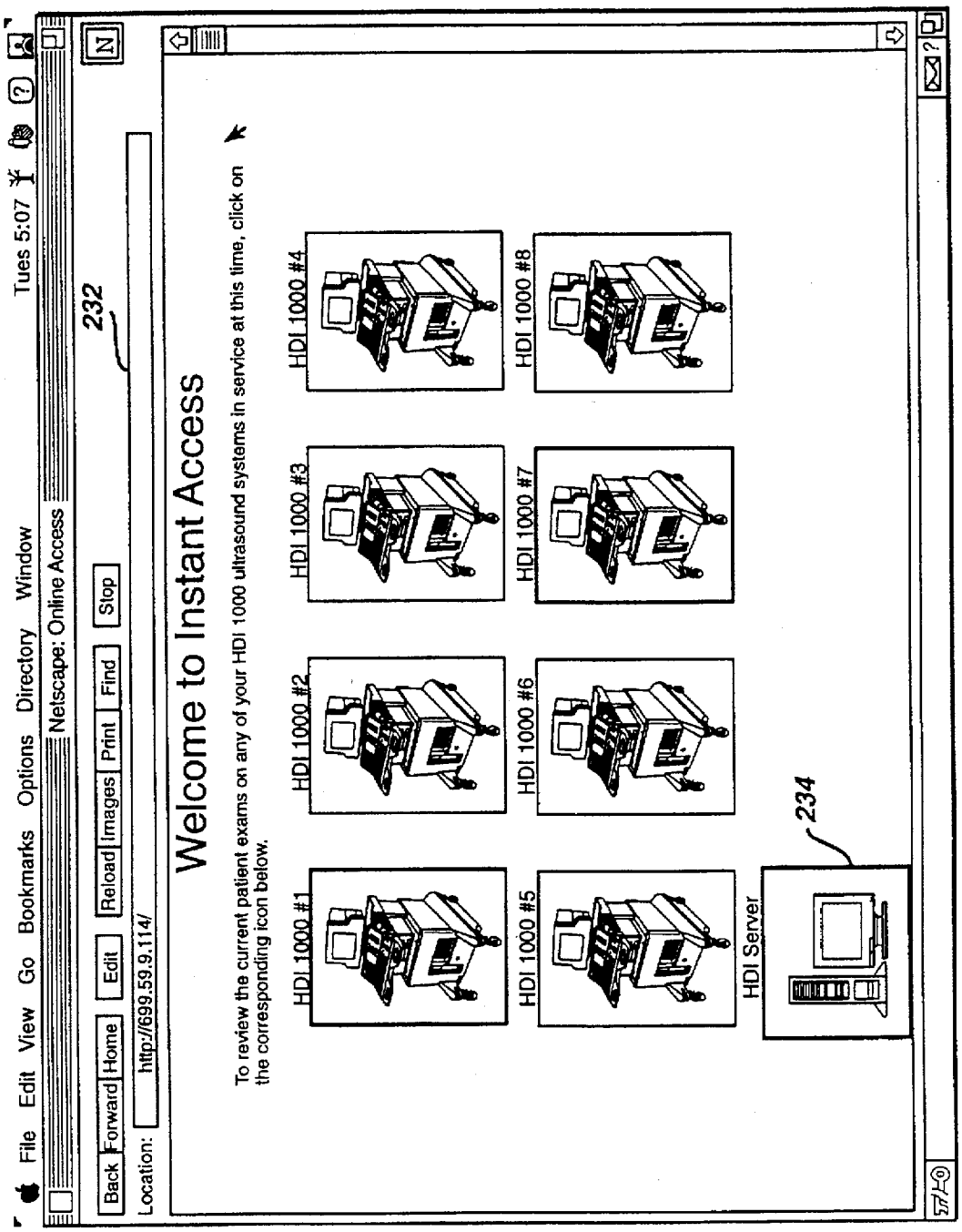
FIG. 11 illustrates a Web home page of a network of ultrasound systems constructed in accordance with the principles of the present invention.
Figure 12:
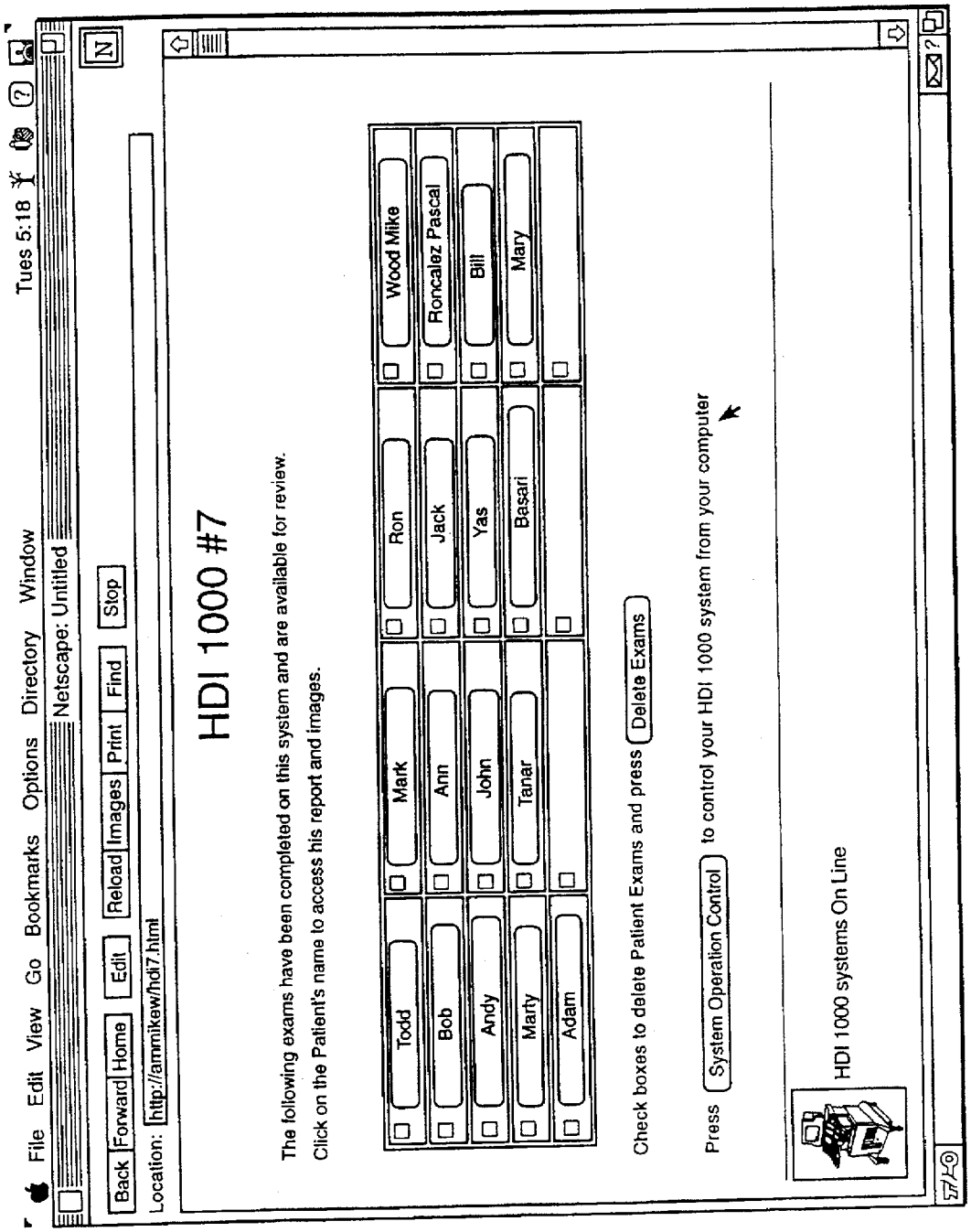
FIG. 12 illustrates a patient directory Web page of one system of the network of ultrasound systems which is accessed through the network home page of FIG. 11.
Figure 13:
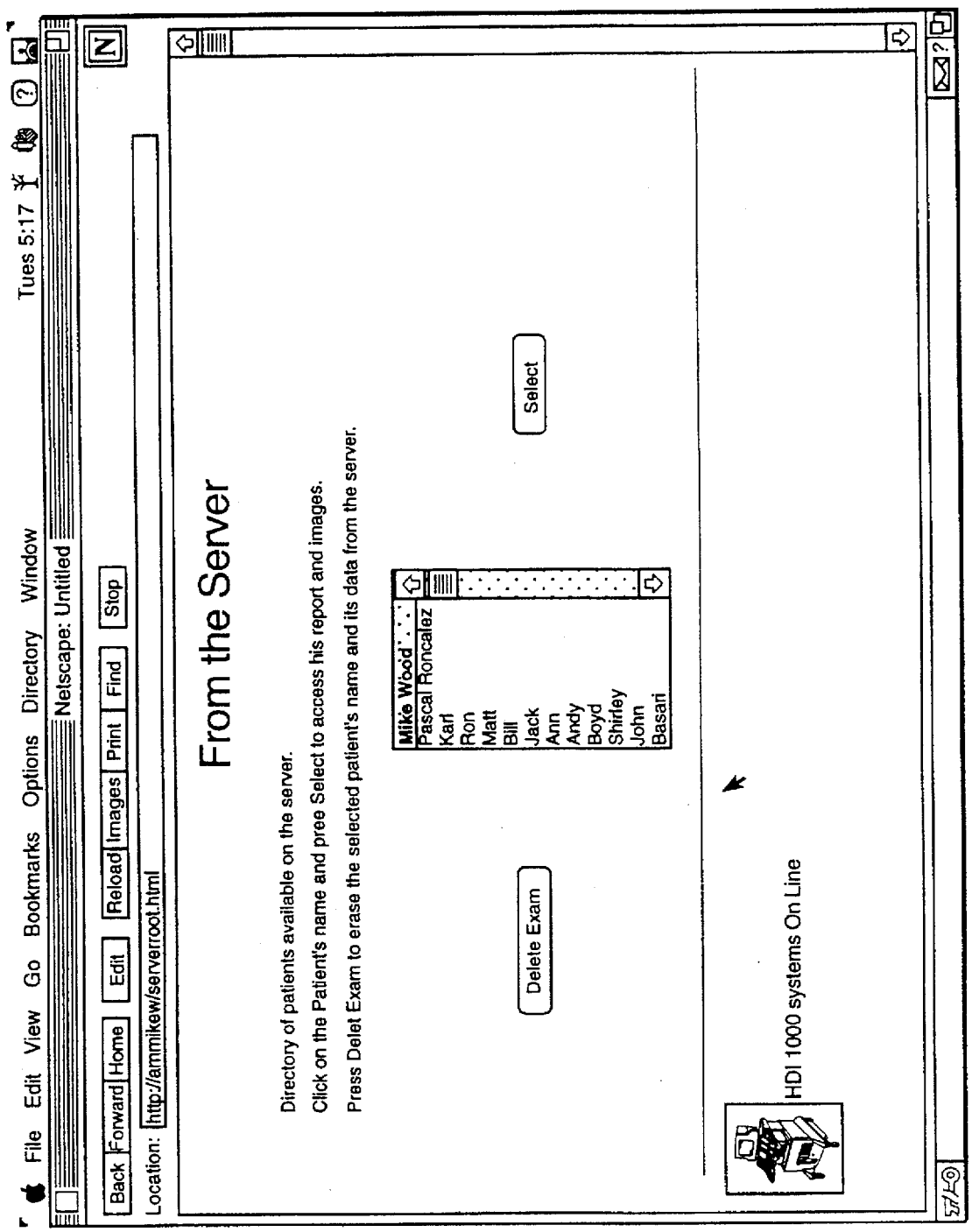
FIG. 13 illustrates another patient directory Web page of a central server which is accessed through the network home page of FIG. 11.
Figure 14:
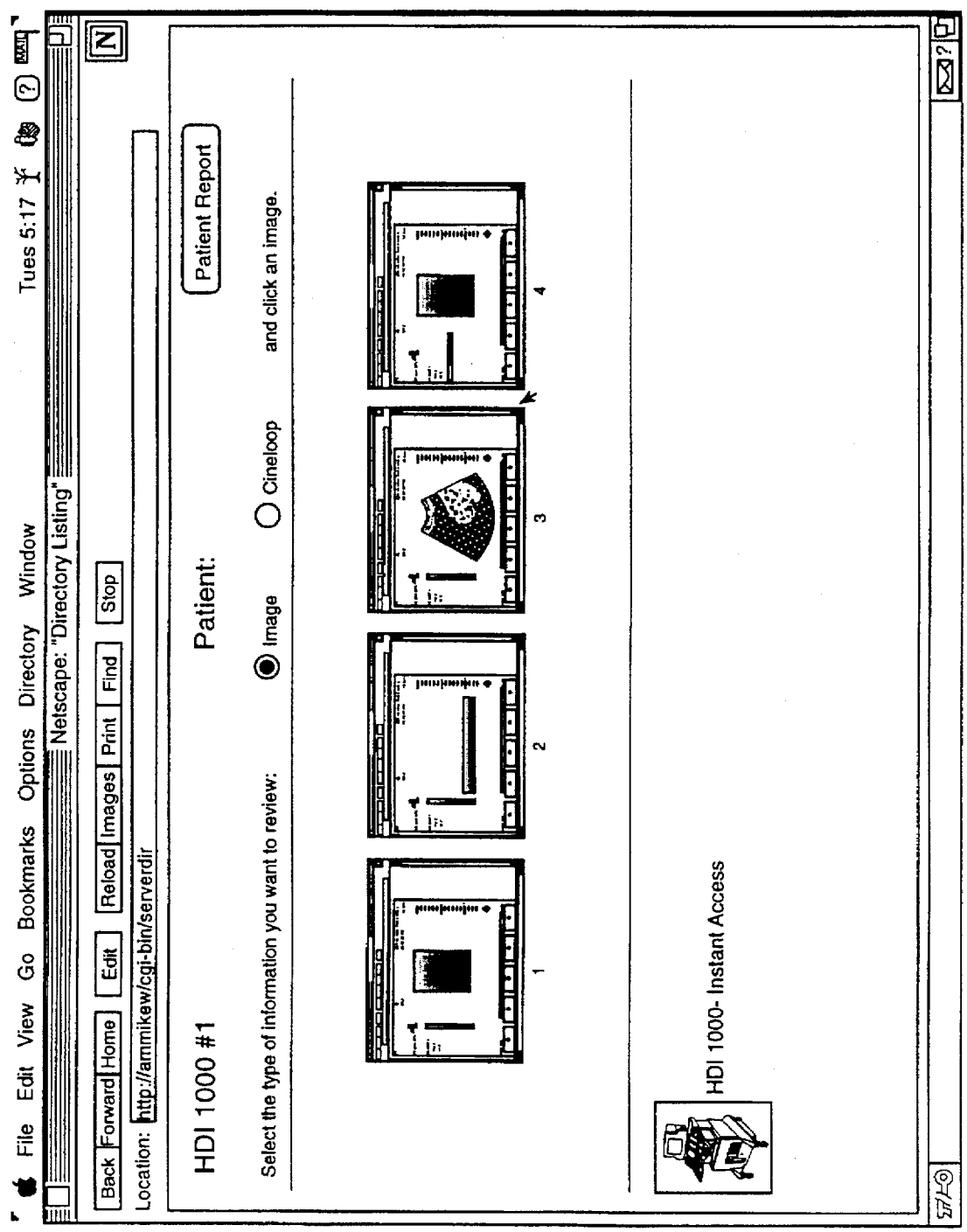
FIG. 14 illustrates a patient directory Web page of one of the systems on a network which is accessed through the network patient directory Web page of FIG. 13.

The foregoing Web browser screens were acquired from the network server of an individual ultrasound system. As indicated above, it is also possible to connect a number of ultrasound systems in a local network which utilizes a single server connected to the Internet. The local network server includes the communication elements 30, 31, 34, 36, 46 and 48 of the ultrasound system of FIG. 2. The Web homepage of such a local network of ultrasound systems is shown in FIG. 11. As the Netscape address bar shows, the remote terminal user's Web browser is accessing the IP address 699.59.9.114 of the HDI Server for the local network. The HDI Server 234 is the only machine with a connection to and address on the Internet; the ultrasound systems all have subnetwork addresses on the local network, such as hdi1, hdi2, hdi3, etc., which are administered by the HDI Server 234. The local network server is depicted in the lower graphic 234' of the homepage, and above the server are graphics for eight ultrasound systems connected to the local network. Two of the ultrasound systems, HDI 1000 #1 and HDI 1000 #7, are seen to be highlighted with a solid border. This highlighting appears as a bright color on the Web browser screen and indicates that these two systems are currently active on the local network. Clicking on either of them will take the remote terminal user to the homepage for the selected system. Clicking the graphic for HDI 1000 #7 system will execute an HREF link on the local network server to the HTTP server of the HDI 1000 #7 system, which will return the system homepage as shown in FIG. 12. From this homepage for the #7 system the remote terminal user can access patient reports and images, delete exams from system storage, perform system diagnostics, or connect directly to System Operation Control to control the operation of the HDI 1000 #7 system.

An advantage of the local network is that all systems on the network can utilize the local server to store ultrasound images and patient reports, making them accessible to remotely located diagnosing physicians even when the ultrasound systems are not in operation. When all of the network's ultrasound systems use the HDI Server 234 for storage of their diagnostic results, all of this information will be accessible over the Internet even when the ultrasound systems are disconnected for use elsewhere or turned off at the end of a day. A remote user terminal can connect to the HTTP server 30 of the HDI Server 234 and, at the homepage of FIG. 11, click on the HDI Server graphic 234 to take the remote user to the patient directory Web page shown in FIG. 13. This patient directory page lists the names of all patients with reports or images stored on the local network HDI Server 234, and the identity of the ultrasound system on which the patient was examined. The remote terminal user can click on a patient's name to access the reports and ultrasound images from that patient's exams, or delete the patient's records from the HDI Server 234 after they have been reviewed by the physician or archived. At the bottom of the screen the user is able to link to the ultrasound systems which are presently active on the local network. If the remote terminal user Selects the name of a patient on the Web page of FIG. 13, the images and reports of the selected patient are retrieved and displayed by the local network server as shown by the patient directory screen of FIG. 14. As in the case of the Web page of FIG. 5, hypertext links are made to ultrasound images and reports from the patient directory page.

Figure 15:
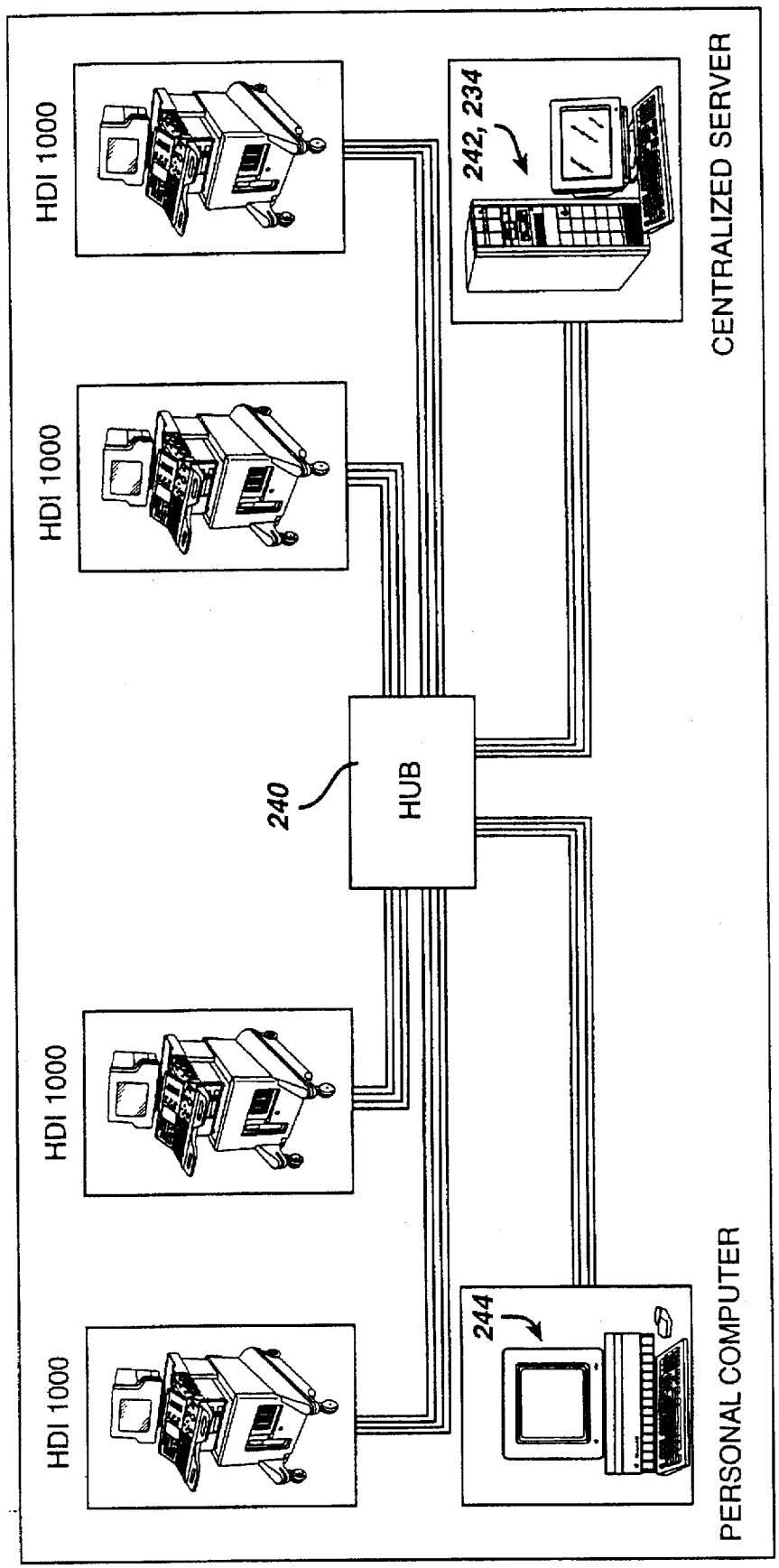
FIG. 15 illustrates in block diagram form a local network of ultrasound systems.
Figure 16:
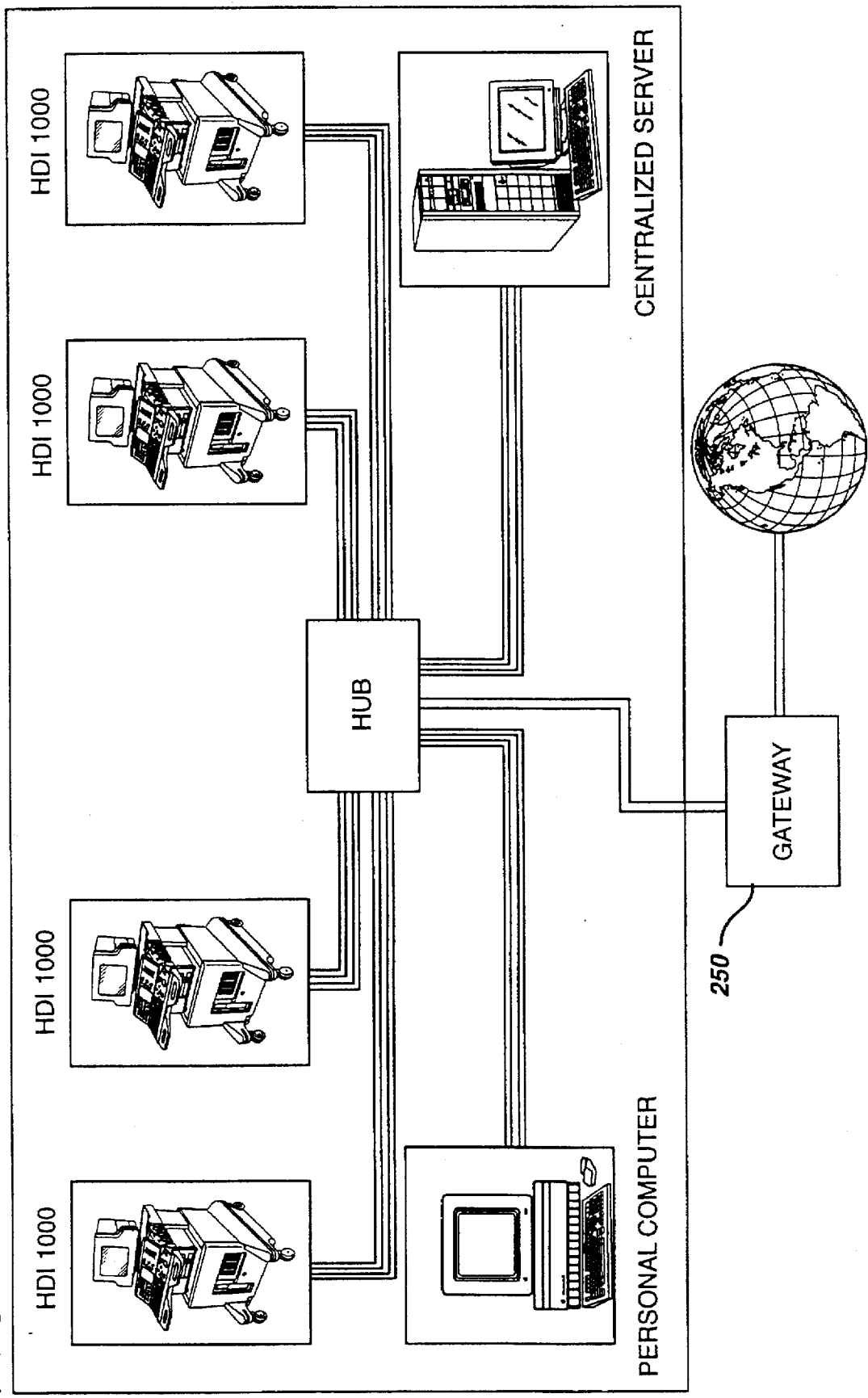
FIG. 16 illustrates in block diagram form a local network of ultrasound systems connected by a gateway to the Internet.
Figure 17:
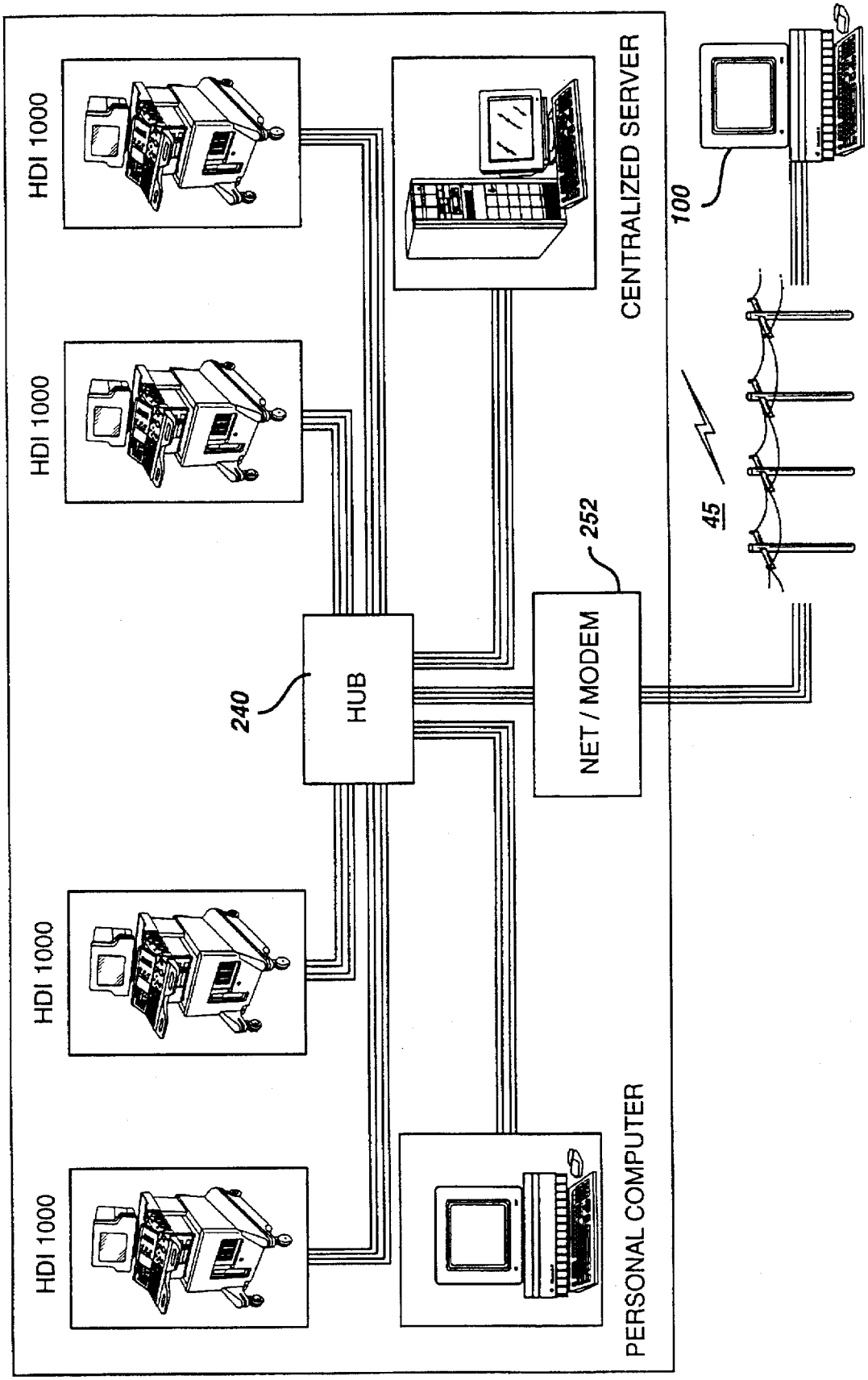
FIG. 17 illustrates in block diagram form a local network of ultrasound systems connected by a network modem to a personal computer remote from the network.

A number of local ultrasound network configurations are shown in FIGS. 15–17. In FIG. 15, four ultrasound systems, a personal computer 244, and a local network server 242 are connected in a local network by a hub 240. The hub 240 is a simple device for interconnecting several serial data lines and is commercially available for a cost of about $250 from Farallon Corporation. The local network server 242 hardware can be no more than a personal computer with the network communications elements listed above and with extended storage for retention of a large volume of ultrasound images and reports stored by the network's ultrasound systems. A user at the personal computer 244 can access the local network server and individual active ultrasound systems of this local network, or "intranetwork", in the same manner as described above for the externally accessible "internetwork."

The network arrangement of FIG. 16 is similar to that of FIG. 15, except that the local network is now Internet accessible through a gateway 250. Since it is expected that most physicians will not want to administer and maintain their own gateways and routers, the gateway will most commonly be effected through modem or high data rate connection to an Internet service provider. For a low monthly service charge the Internet service provider can deal with the internetworking intricacies in which the physician has great reliance but little operational interest.

Finally, FIG. 17 illustrates a network configuration by which a physician can directly access his ultrasound system network, with or without the Internet. The hub 240 is connected to a net/modem 252 which can be accessed over wireless or telephone networks 40 from a remote personal computer 100. Using high level communication protocols such as File Transfer Protocol (FTP) or Network File Sharing (NFS) which use the lower level TCP/IP as a foundation, the physician can dial into his network directly and access diagnostic information, without the need for Internet access. For users who require only specific limited access to their ultrasound system networks, the arrangement of FIG. 17 provides an easy and secure means for a physician to remotely access his ultrasound system network and its information.

The Internet and World Wide Web ultrasound capabilities of the present invention, when embodied in the form of software, can be easily installed as an upgrade to an existing ultrasound system without these capabilities, either by directly installing the software in the ultrasound system and connecting a modem or network hardware. Installation of the software upgrade can even be done remotely as described in U.S. Pat. No. 5,603,323, or simple instructions given to the ultrasound system owner by the system manufacturer to enable the owner to install the capability himself.

TABLE 1

```
/*
** $Filename: patdir.c $
**
** (C) Copyright 1996 Advanced Technology Labs
**     All Rights Reserved
**
#include <exec/types.h>
#include <dos/dos.h>
#include <stdio.h>
main(int argc,char **argv)
    {
    ULONG h_count,i;
    h_count = 0;
    if(Open_Resources ( ))
    {
        /* Header */
        /*------*/
        printf("Content-type: text/html%c%c",10,10);
        printf ("<HTML>\n");
        printf ("<BODY>\n");
        ...
        /* For each of the *.gif files that were saved, display */
        /* a thumbnail image on the browser.                    */
        /*----------------------------------------------*/
        for (i=0;i<Count;i++)
        {
            if(h_count == 0)
            {
                printf ("<TR><TD ALIGN=\"CENTER\" VALIGN=\"BOTTOM\" WIDTH=78>\n") ;
            }
```

TABLE 1-continued

```
        else
        {
          printf("<TD ALIGN=\"CENTER\" VALIGN=\"BOTTOM\" WIDTH=98>\n");
        }
        printf("<H6><CENTER><A HREF=\"dispimage?recall/DAT_SR_%d.gif\">\n", (i+1));
        printf("<IMG SRC=\"%/recall/DAT_SR_%d.gif\" ALT=\"Image %d\"></A>\n", (i+1), (i+1));
        printf("<BR>%d</CENTER></H6></TD>\n", (i+1));
        h_count++;
        if(h_count == 6)
        {
          printf ("</TR>\n");
          h_count = 0;
        }
        . . .
        /* Header Tail */
        /*----------*/
        printf ("</BODY>\n");
        printf ("</HTML>\n");
      }
Close_Resources ( );
}
```

What is claimed is:

1. A medical diagnostic ultrasound system which produces and stores diagnostic ultrasound images or diagnostic reports, comprising:
   an HTTP server; and
   means for connecting said HTTP server to a network,
   whereby said images or reports are remotely accessible through said HTTP server.

2. The medical diagnostic ultrasound system of claim 1, wherein said means for connecting said server to a network comprises TCP/IP software.

3. The medical diagnostic ultrasound system of claim 2, wherein said means for connecting said server to a network further comprises PPP software.

4. The medical diagnostic ultrasound system of claim 1, further comprising a stored HTML page and accessible by said server for transmission to a remote terminal.

5. The medical diagnostic ultrasound system of claim 1, further comprising a stored CGI program and accessible by said server.

6. A medical diagnostic ultrasound system which produces and stores diagnostic ultrasound images or diagnostic reports, said system comprising:
   means for storing diagnostic ultrasound images or diagnostic reports produced by said ultrasound system;
   means for compatibly connecting said ultrasonic diagnostic system to the Internet; and
   means for making said stored diagnostic ultrasound images or diagnostic reports accessible to users through said means for comparably connecting,
   whereby stored ultrasound images or reports are remotely accessible over the Internet.

7. The medical diagnostic ultrasound system of claim 6, wherein said means for compatibly connecting comprises TCP/IP software.

8. The medical diagnostic ultrasound system of claim 7, wherein said means for compatibly connecting further comprises PPP software.

9. The medical diagnostic ultrasound system of claim 6, wherein said means for making stored diagnostic ultrasound images or diagnostic reports accessible includes a server, and further comprising a stored HTML page and accessible by said server for transmission to a remote terminal.

10. The medical diagnostic ultrasound system of claim 9, further comprising a stored CGI program and accessible by said server.

11. The medical diagnostic ultrasound system of claim 6, wherein said means for compatibly connecting comprises network equipment, including a connection to the Internet, connected to said ultrasound system.

12. The medical diagnostic ultrasound system of claim 11, wherein said network equipment includes a Web server.

13. The medical diagnostic ultrasound system of claim 12, wherein said Web server comprises an HTTP server.

14. The medical diagnostic ultrasound system of claim 12, wherein said network equipment includes said means for storing said diagnostic ultrasound images or diagnostic reports produced by said ultrasound system.

15. The medical diagnostic ultrasound system of claim 12, wherein said Web server includes communications hardware and software for providing Web pages over the Internet which provide access to an image of said ultrasound system over the Internet.

16. The medical diagnostic ultrasound system of claim 15, wherein said communications hardware or software includes HTML page software.

17. The medical diagnostic ultrasound system of claim 15, wherein said communications hardware or software includes a hyperlink to an ultrasound image file stored by said ultrasound system.

18. The medical diagnostic ultrasound system of claim 17, wherein said network equipment includes said means for storing said diagnostic ultrasound images or diagnostic reports produced by said ultrasound system; and wherein said ultrasound image file is stored on said network equipment by said ultrasound system.

19. A medical diagnostic ultrasound system which produces and stores diagnostic ultrasound images or diagnostic reports, said system comprising:
   a connection to a network; and
   means for transmitting Web data over said network which provides access over the World wide Web to ultrasound images or reports stored by said ultrasonic diagnostic system,
   whereby ultrasound images or reports stored on said system are remotely accessible over said network.

20. The medical diagnostic ultrasound system of claim 19, wherein said means for transmitting Web data over said network comprises an HTTP server.

21. The medical diagnostic ultrasound system of claim 20, wherein said means for transmitting Web data over said network further comprises a stored HTML page.

22. The medical diagnostic ultrasound system of claim 19, wherein said means for transmitting Web date comprises network equipment connected to said ultrasound system.

23. The medical diagnostic ultrasound system of claim 22, wherein said network equipment includes a Web server.

24. The medical diagnostic ultrasound system of claim 23, wherein said Web server comprises an HTTP server.

25. The medical diagnostic ultrasound system of claim 23, wherein said network equipment includes means for storing said diagnostic ultrasound images or diagnostic reports produced by said ultrasound system.

26. The medical diagnostic ultrasound system of claim 23, wherein said Web server includes communications hardware and software for providing Web pages over the Internet which provide access to an image of said ultrasound system over the Internet.

27. The medical diagnostic ultrasound system of claim 26, wherein said communications hardware or software includes HTML page software.

28. The medical diagnostic ultrasound system of claim 26, wherein said communications hardware or software includes a hyperlink to an ultrasound image file stored by said ultrasound system.

29. The medical diagnostic ultrasound system of claim 28, wherein said network equipment includes means for storing said diagnostic ultrasound images or diagnostic reports produced by said ultrasound system; and wherein said ultrasound image file is stored on said network equipment by said ultrasound system.

30. A medical diagnostic ultrasound system which produces and stores diagnostic ultrasound images or diagnostic reports, said system comprising:

means for storing diagnostic ultrasound images or diagnostic reports produced by said ultrasound system;

a connection to a network; and a CGI program for translating diagnostic ultrasound images or diagnostic reports stored by said ultrasound system to said network connection.

31. The medical diagnostic ultrasound system of claim 30, wherein said CGI program comprises means for accessing ultrasound image or diagnostic report files for access over said network connection.

32. The medical diagnostic ultrasound system of claim 30, wherein said CGI program comprises means for accessing diagnostic information of said ultrasound system over said network connection.

33. The medical diagnostic ultrasound system of claim 32, wherein said CGI program comprises means for executing ultrasound system diagnostic software of said ultrasound system over said network connection.

34. A medical diagnostic ultrasound system which produces and stores diagnostic ultrasound images or diagnostic reports, said system comprising:

means for storing diagnostic ultrasound images or diagnostic reports produced by said ultrasound system;

a connection to a network;

means for transmitting a screen display over said network connection from said ultrasound system in which are embedded hypertext links to said diagnostic ultrasound images or diagnostic reports, whereby ultrasound images or reports stored on said system are remotely accessible over said network.

35. The medical diagnostic ultrasound system of claim 6, 30, or 34, wherein said means for storing comprises digital memory located on said ultrasound system.

36. The medical diagnostic ultrasound system of claim 6, 30, or 34, wherein said means for storing comprises digital memory remotely located from said ultrasound system and connected to said ultrasound system by a network connection.

37. The medical diagnostic ultrasound system of claim 36, wherein said means for storing comprises a terminal including a network server.

38. The medical diagnostic ultrasound system of claim 34, wherein said means for transmitting a screen display comprises network equipment connected to said ultrasound system.

39. The medical diagnostic ultrasound system of claim 38, wherein said network equipment includes a server.

40. The medical diagnostic ultrasound system of claim 39, wherein said server comprises an HTTP server.

41. The medical diagnostic ultrasound system of claim 40, wherein said HTTP server includes communications hardware and software for providing Web pages over the Internet which provide access to an image of said ultrasound system over the Internet.

42. The medical diagnostic ultrasound system of claim 39, wherein said network equipment includes said means for storing said diagnostic ultrasound images or diagnostic reports produced by said ultrasound system; and wherein said embedded hypertext links provide links to images or reports stored on said network equipment.

43. A medical diagnostic ultrasound system, comprising:

means for producing a screen display including an image of a control of said ultrasound system;

means for connecting said ultrasound system to a remote terminal; and means for transmitting said screen display to said remote terminal, whereby said screen display can be used by a user at said remote terminal to control said ultrasound system.

44. The medical diagnostic ultrasound system of claim 43, wherein said screen display comprises means for controlling the mode of said ultrasound system from said remote terminal.

45. The medical diagnostic ultrasound system of claim 43, wherein said screen display comprises means for controlling an image display parameter of said ultrasound system from said remote terminal.

46. A medical diagnostic ultrasound system which produces and stores diagnostic ultrasound images or diagnostic reports, comprising:

server software installed on said ultrasound system; and means for connecting said server software to a network, whereby said images or reports are remotely accessible through said server software.

47. The medical diagnostic ultrasound system of claim 46, further comprising a stored HTML page and accessible by said server for transmission to a remote terminal.

48. The medical diagnostic ultrasound system of claim 47, further comprising a stored CGI program and accessible by said server.

49. The medical diagnostic ultrasound system of claim 19, 30, 34 or 46 wherein said connection to a network comprises a serial port.

50. The medical diagnostic ultrasound system of claim 49, wherein said connection to a network further comprises TCP/IP software.

51. The medical diagnostic ultrasound system of claim 50, wherein said connection to a network further comprises PPP software.

52. A medical diagnostic ultrasound system which and stores diagnostic ultrasound images or diagnostic reports, comprising:

network software installed on said ultrasound system for communicating with a remote terminal;

server software installed on said ultrasound system and in communication with said network software;

HTML page software stored on said system; and a CGI program accessible by said server software and accessing diagnostic ultrasound images or diagnostic reports of said ultrasound system for transmission by said server software to said remote terminal.

53. The medical diagnostic ultrasound system of claim 52, wherein said network software comprises TCP/IP software.

54. The medical diagnostic ultrasound system of claim 53, wherein said network software further comprises PPP software.

55. The medical diagnostic ultrasound system of claim 52, wherein said HTML page software is accessible by said server software for transmission of an ultrasound image or diagnostic report to a remote terminal.

56. The medical diagnostic ultrasound system of claim 4, 9, 21, 47, or 55, wherein said HTML page further comprises a hyperlink to an ultrasound image file stored by said ultrasound system.

57. The medical diagnostic ultrasound system of claim 4, 9, 21, 47 or 55, wherein said HTML page further comprises a hyperlink to an ultrasound diagnostic report file stored by said ultrasound system.

58. The medical diagnostic ultrasound system of claim 4, 9, 21, 47 or 55, wherein said HTML page further comprises a hyperlink to an ultrasound system diagnostic file stored by said ultrasound system.

59. The medical diagnostic ultrasound system of claim 4, 9, 21, 47 or 55, wherein said HTML page further comprises a hyperlink to a patient directory stored by said ultrasound system.

60. The medical diagnostic ultrasound system of claim 4, 9, 21, 47 or 55, wherein said HTML page further comprises a hyperlink to an ultrasound system control display screen stored by said ultrasound system.

61. A medical diagnostic ultrasound system network comprising:

a plurality of ultrasound systems, each including internal network communications software and network server software for accessing diagnostic ultrasound images or diagnostic reports produced by said ultrasound system; and means for connecting said ultrasound systems in a network, wherein said diagnostic ultrasound images or diagnostic reports produced by said ultrasound systems are accessible over said network.

62. The medical diagnostic ultrasound system network of claim 61, further comprising a terminal, connected to said network, for accessing diagnostic ultrasound images or diagnostic reports produced by said ultrasound systems.

63. The medical diagnostic ultrasound system network of claim 62, wherein said terminal is connected to said ultrasound system network by means for connecting to a local network.

64. The medical diagnostic ultrasound system network of claim 62, wherein said terminal is connected to said ultrasound system network from a remote location.

65. The medical diagnostic ultrasound system network of claim 64, wherein said remote terminal is connected to said ultrasound system network by a modem.

66. The medical diagnostic ultrasound system network of claim 62, wherein said remote terminal includes a Web browser for communicating with said ultrasound system network.

67. The medical diagnostic ultrasound system network of claim 61, further comprising a central storage device including network communications software for storing diagnostic ultrasound images or diagnostic reports produced by said ultrasound systems.

68. The medical diagnostic ultrasound system network of claim 67, wherein said central storage device further includes network server software for accessing diagnostic ultrasound images or diagnostic reports stored on said storage device from a remote terminal.

* * * * *